(12) United States Patent
Yang et al.

(10) Patent No.: US 7,947,072 B2
(45) Date of Patent: May 24, 2011

(54) TWO-PART EXPANDABLE HEART VALVE

(75) Inventors: Jibin Yang, Aliso Viejo, CA (US); Matthew L. Pease, Mountain View, CA (US); Brandon G. Walsh, Livermore, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 689 days.

(21) Appl. No.: 11/749,722

(22) Filed: May 16, 2007

(65) Prior Publication Data

US 2007/0255398 A1    Nov. 1, 2007

Related U.S. Application Data

(63) Continuation of application No. 10/653,843, filed on Sep. 2, 2003, now Pat. No. 7,276,084, which is a continuation of application No. 09/815,521, filed on Mar. 23, 2001, now Pat. No. 6,733,525.

(51) Int. Cl.
*A61F 2/24* (2006.01)

(52) U.S. Cl. ...................................... 623/1.26; 623/2.17

(58) Field of Classification Search .................. 623/1.24, 623/1.26, 2.1–2.4, 900, 1.17, 1.22
See application file for complete search history.

(56) References Cited

U.S. PATENT DOCUMENTS

| | | | |
|---|---|---|---|
| 3,409,013 A | 11/1968 | Berry | |
| 3,671,979 A | 6/1972 | Moulopoulos | |
| 4,056,854 A | 11/1977 | Boretos et al. | |
| 4,106,129 A | 8/1978 | Carpentier et al. | |
| 4,297,749 A | 11/1981 | Davis et al. | |
| 4,878,906 A | 11/1989 | Lindemann et al. | |
| 4,922,905 A | 5/1990 | Strecker | |
| 4,960,424 A | 10/1990 | Grooters | |
| 4,994,077 A | 2/1991 | Dobben | |
| 5,078,726 A | 1/1992 | Kreamer | |
| 5,123,917 A | 6/1992 | Lee | |
| 5,147,370 A | 9/1992 | McNamara et al. | |
| 5,163,953 A | 11/1992 | Vince | |
| 5,266,073 A | 11/1993 | Wall | |
| 5,306,294 A | 4/1994 | Winston et al. | |
| 5,332,402 A | 7/1994 | Teitelbaum | |

(Continued)

FOREIGN PATENT DOCUMENTS

DE    036 40 742 A1    6/1987
DE    198 57 887 A1    7/2000

(Continued)

*Primary Examiner* — Corrine McDermott
*Assistant Examiner* — Cheryl Miller
(74) *Attorney, Agent, or Firm* — David L. Hauser; Guy Cumberbatch

(57) ABSTRACT

Expandable heart valves for minimally invasive valve replacement surgeries are disclosed. The valves are rolled into a first, contracted configuration for minimally invasive delivery and then unrolled or unfurled at the implantation site. One- and two-piece stents may be used in conjunction with a plurality of flexible leaflet-forming membranes. The one-piece stents may include an annulus anchoring section, a sinus section with the membranes attached over sinus apertures, and a rigid outflow section. The two-piece stent may include a primary stent to provide a tubular base at the annulus, and a secondary stent having the membranes that couples within the primary stent. Lockout tabs to secure the stents in their expanded shapes are provided. Also, alignment structure may be provided to ensure concentric unfurling. Anchoring barbs at the stent edges or in the stent body secure the valve within the annulus. Methods of implantation are also provided.

18 Claims, 17 Drawing Sheets

U.S. PATENT DOCUMENTS

| | | | |
|---|---|---|---|
| 5,344,426 A | 9/1994 | Lau et al. | |
| 5,366,473 A | 11/1994 | Winston et al. | |
| 5,370,685 A | 12/1994 | Stevens | |
| 5,397,351 A | 3/1995 | Pavenik et al. | |
| 5,411,552 A | 5/1995 | Andersen et al. | |
| 5,443,500 A | 8/1995 | Sigwart | |
| 5,545,214 A | 8/1996 | Stevens | |
| 5,554,185 A | 9/1996 | Block et al. | |
| 5,556,413 A | 9/1996 | Lam | |
| 5,593,434 A | 1/1997 | Williams | |
| 5,607,465 A | 3/1997 | Camilli | |
| 5,618,299 A | 4/1997 | Khosravi et al. | |
| 5,634,941 A | 6/1997 | Winston et al. | |
| 5,682,906 A | 11/1997 | Sterman et al. | |
| 5,713,951 A | 2/1998 | Garrison et al. | |
| 5,716,370 A | 2/1998 | Williamson, IV et al. | |
| 5,723,003 A | 3/1998 | Winston et al. | |
| 5,728,151 A | 3/1998 | Garrison et al. | |
| 5,752,526 A | 5/1998 | Cosgrove | |
| 5,769,812 A | 6/1998 | Stevens et al. | |
| 5,810,847 A | 9/1998 | Laufer et al. | |
| 5,810,870 A | 9/1998 | Myers et al. | |
| 5,824,046 A | 10/1998 | Smith et al. | |
| 5,824,064 A | 10/1998 | Taheri | |
| 5,840,081 A | 11/1998 | Andersen et al. | |
| RE35,988 E | 12/1998 | Winston et al. | |
| 5,855,597 A | 1/1999 | Jayaraman | |
| 5,855,601 A | 1/1999 | Bessler et al. | |
| 5,873,907 A | 2/1999 | Frantzen | |
| 5,876,419 A | 3/1999 | Carpenter et al. | |
| 5,910,170 A | 6/1999 | Reimink et al. | |
| 5,925,063 A * | 7/1999 | Khosravi | 606/200 |
| 5,957,949 A | 9/1999 | Leonhardt et al. | |
| 5,984,963 A | 11/1999 | Ryan et al. | |
| 5,993,489 A | 11/1999 | Lewis et al. | |
| 6,010,531 A | 1/2000 | Donlon et al. | |
| 6,015,430 A | 1/2000 | Wall | |
| 6,027,516 A | 2/2000 | Kolobow et al. | |
| 6,027,525 A | 2/2000 | Suh et al. | |
| 6,042,607 A | 3/2000 | Williamson, IV et al. | |
| 6,048,360 A | 4/2000 | Khosravi et al. | |
| 6,074,418 A | 6/2000 | Buchanan et al. | |
| 6,083,219 A | 7/2000 | Laufer | |
| 6,092,529 A | 7/2000 | Cox | |
| 6,096,074 A | 8/2000 | Pedros | |
| 6,099,498 A | 8/2000 | Addis | |
| 6,102,943 A | 8/2000 | McGuinness | |
| 6,106,550 A | 8/2000 | Magovern et al. | |
| 6,162,208 A | 12/2000 | Hipps | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,203,553 B1 | 3/2001 | Robertson et al. | |
| 6,221,091 B1 | 4/2001 | Khosravi | |
| 6,269,819 B1 | 8/2001 | Oz et al. | |
| 6,283,127 B1 | 9/2001 | Sterman et al. | |
| 6,287,334 B1 | 9/2001 | Moll et al. | |
| 6,287,339 B1 | 9/2001 | Vazquez et al. | |
| 6,309,382 B1 | 10/2001 | Garrison et al. | |
| 6,309,417 B1 | 10/2001 | Spence et al. | |
| 6,319,281 B1 | 11/2001 | Patel | |
| 6,425,916 B1 | 7/2002 | Garrison et al. | |
| 6,454,794 B1 | 9/2002 | Knudson et al. | |
| 6,454,799 B1 * | 9/2002 | Schreck | 623/2.18 |
| 6,530,952 B2 | 3/2003 | Vesely | |
| 6,733,525 B2 | 5/2004 | Yang et al. | |
| 7,524,330 B2 * | 4/2009 | Berreklouw | 623/1.36 |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0021872 A1 | 9/2001 | Bailey et al. | |
| 2001/0031972 A1 | 10/2001 | Robertson et al. | |
| 2001/0044591 A1 | 11/2001 | Stevens et al. | |
| 2001/0044656 A1 | 11/2001 | Williamson, IV et al. | |
| 2003/0212452 A1 * | 11/2003 | Zadno-Azizi et al. | 623/1.24 |

FOREIGN PATENT DOCUMENTS

| | | |
|---|---|---|
| EP | 0 382 014 A1 | 8/1990 |
| EP | 0 145 166 B2 | 6/1995 |
| EP | 0 592 410 B1 | 10/1995 |
| EP | 0 737 453 A2 | 10/1996 |
| EP | 0 756 853 A1 | 2/1997 |
| EP | 1 057 460 A1 | 12/2000 |
| EP | 1 088 529 A2 | 4/2001 |
| GB | 2 056 023 A | 3/1981 |
| SU | 127508 A1 | 11/1986 |
| WO | WO 91/17720 A1 | 11/1991 |
| WO | WO 96/02212 A1 | 2/1996 |
| WO | WO 96/19159 A1 | 6/1996 |
| WO | WO 97/12563 A1 | 4/1997 |
| WO | WO 97/12565 A1 | 4/1997 |
| WO | WO 97/27799 A1 | 8/1997 |
| WO | WO 97/30659 A1 | 8/1997 |
| WO | WO 98/11846 A1 | 3/1998 |
| WO | WO 98/29057 A1 | 7/1998 |
| WO | WO 98/57599 A2 | 12/1998 |
| WO | WO 98/57599 A3 | 12/1998 |
| WO | WO 99/15112 A1 | 4/1999 |
| WO | WO 99/33414 A1 | 7/1999 |
| WO | WO 00/00107 A1 | 1/2000 |
| WO | WO 00/41632 A1 | 7/2000 |
| WO | WO 00/41652 A1 | 7/2000 |
| WO | WO 00/44313 A1 | 8/2000 |
| WO | WO 00/45874 A1 | 8/2000 |
| WO | WO 00/47139 A1 | 8/2000 |
| WO | WO 00/48533 A1 | 8/2000 |
| WO | WO 00/61034 A1 | 10/2000 |
| WO | WO 01/19285 A1 | 3/2001 |
| WO | WO 01/26586 A1 | 4/2001 |
| WO | WO 01/52775 A1 | 7/2001 |
| WO | WO 01/54625 A1 | 8/2001 |
| WO | WO 01/56512 A1 | 8/2001 |
| WO | WO 01/62189 A1 | 8/2001 |
| WO | WO 01/64137 A1 | 9/2001 |

* cited by examiner

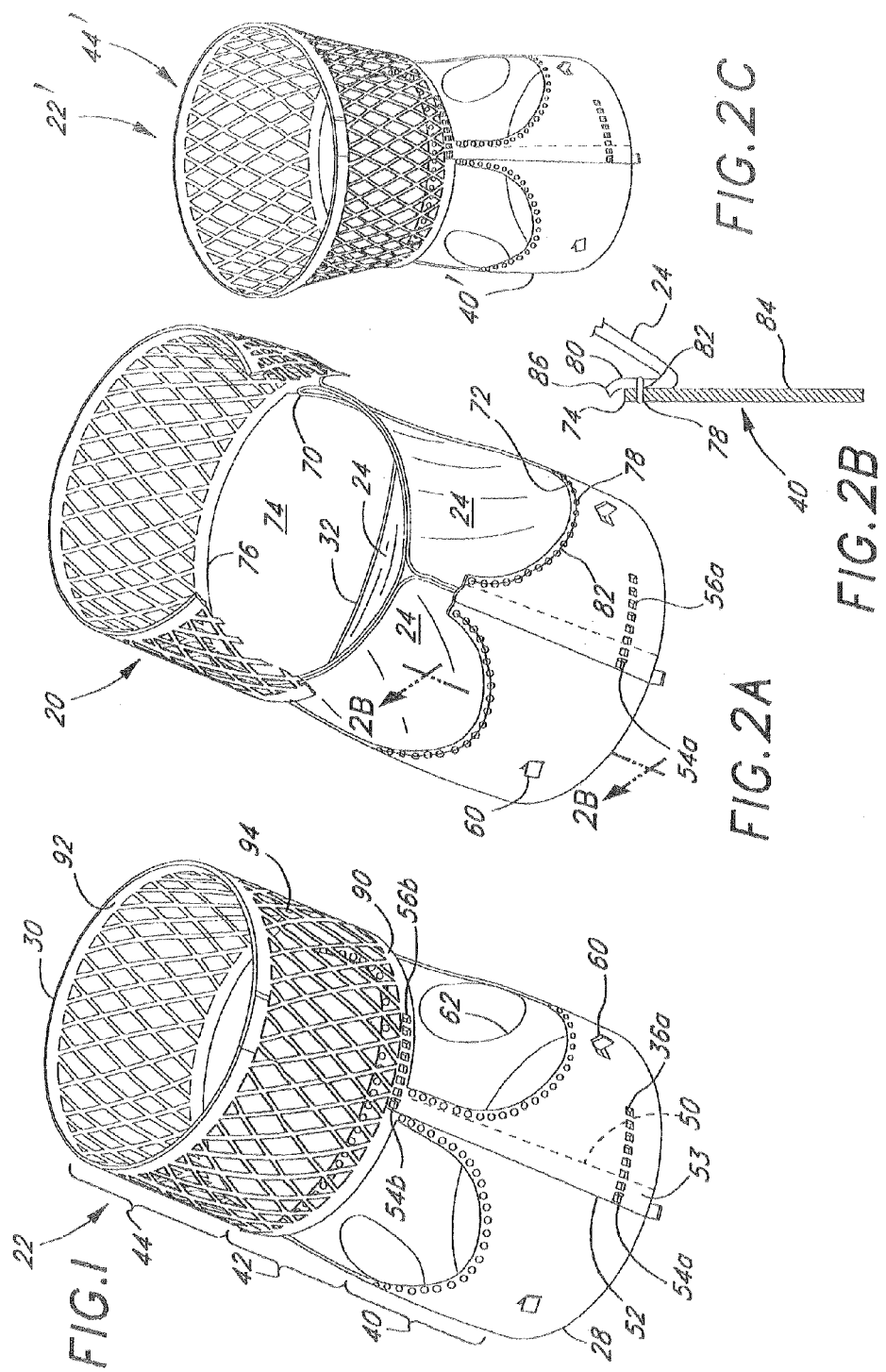

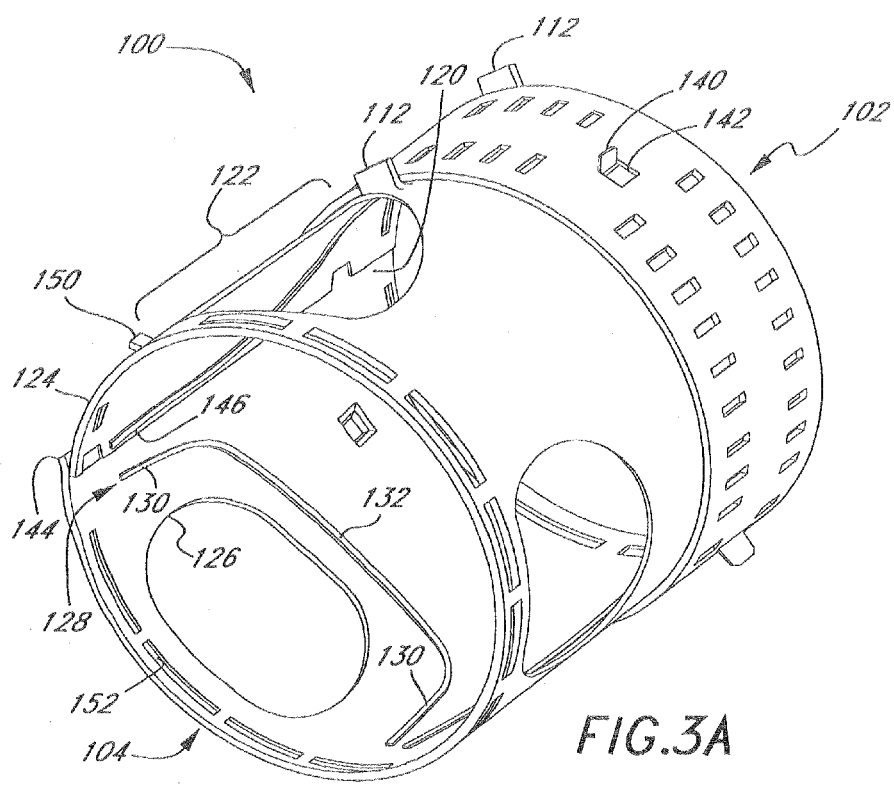
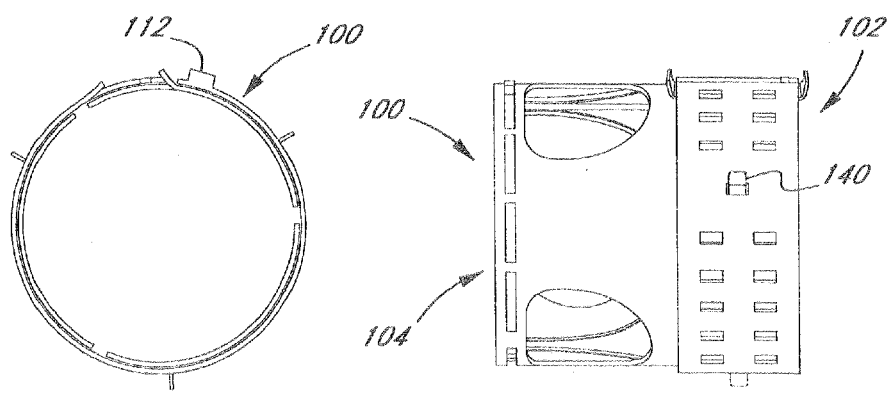
FIG.3A
FIG.3B
FIG.3C

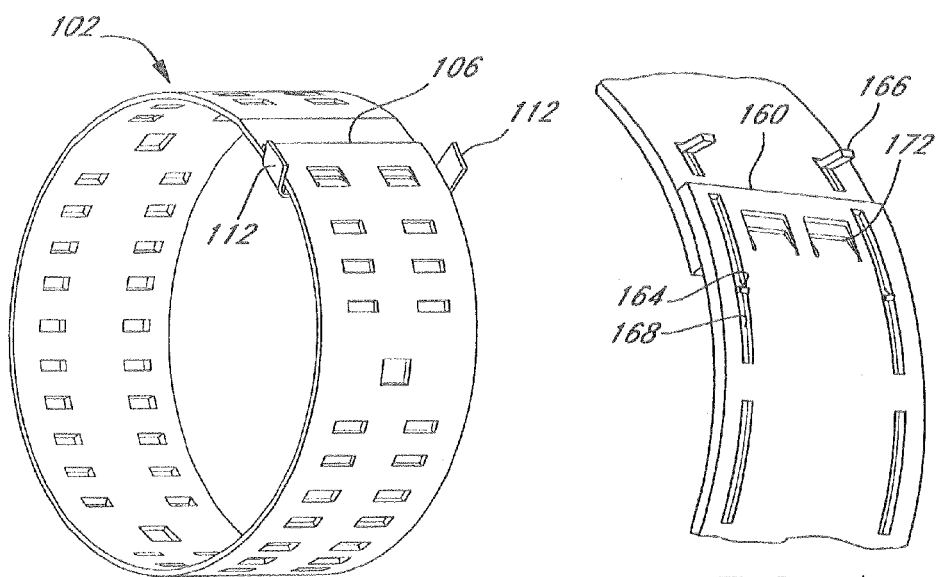
FIG.4A
FIG.5A
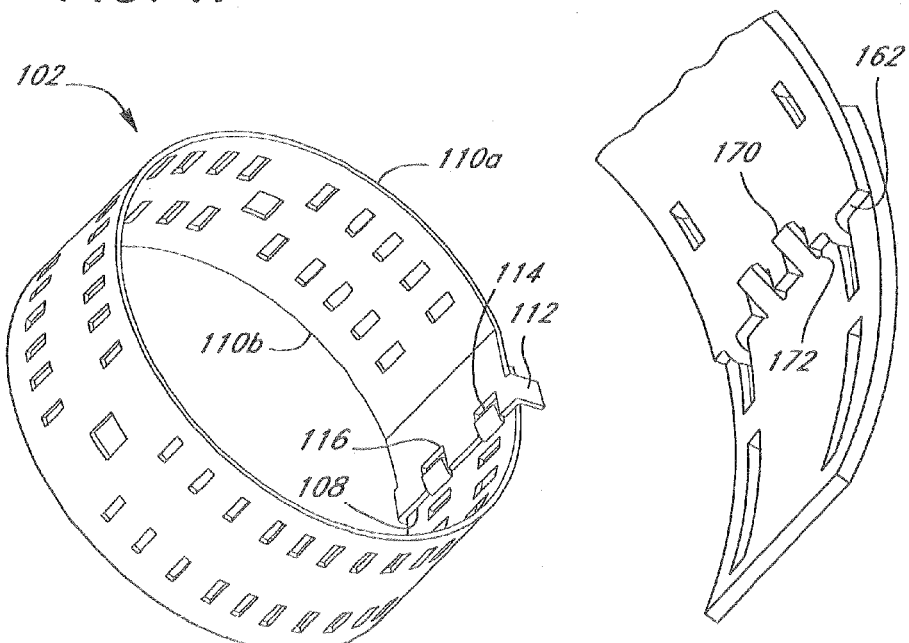
FIG.4B
FIG.5B

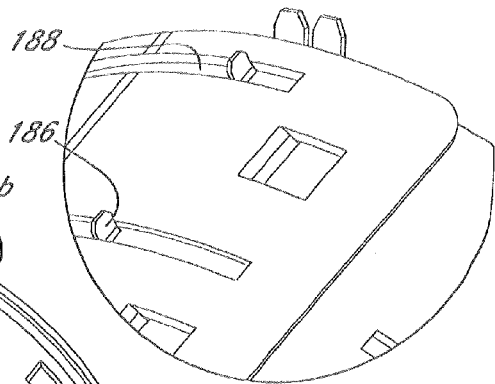
FIG.6C
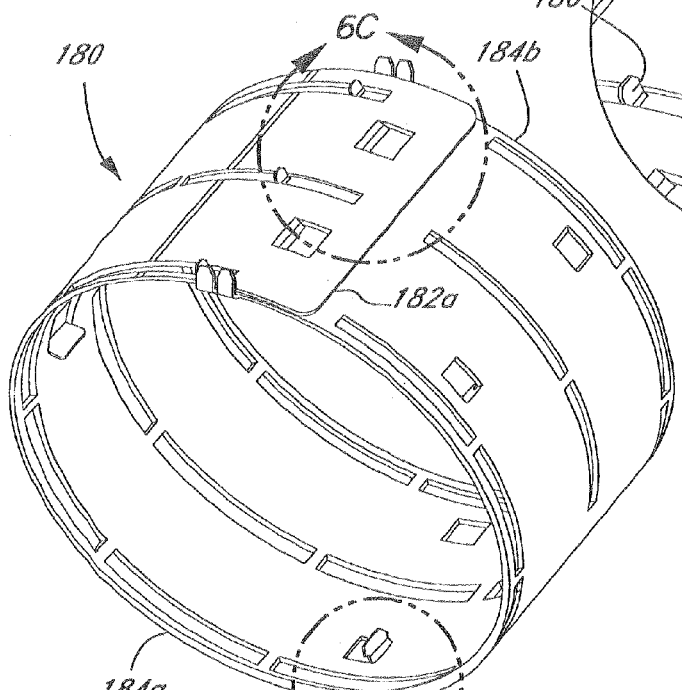
FIG.6A
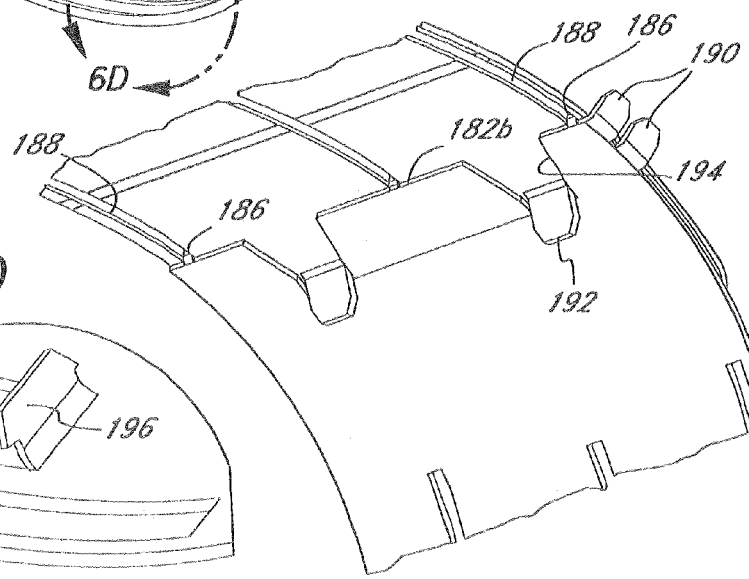
FIG.6B
FIG.6D

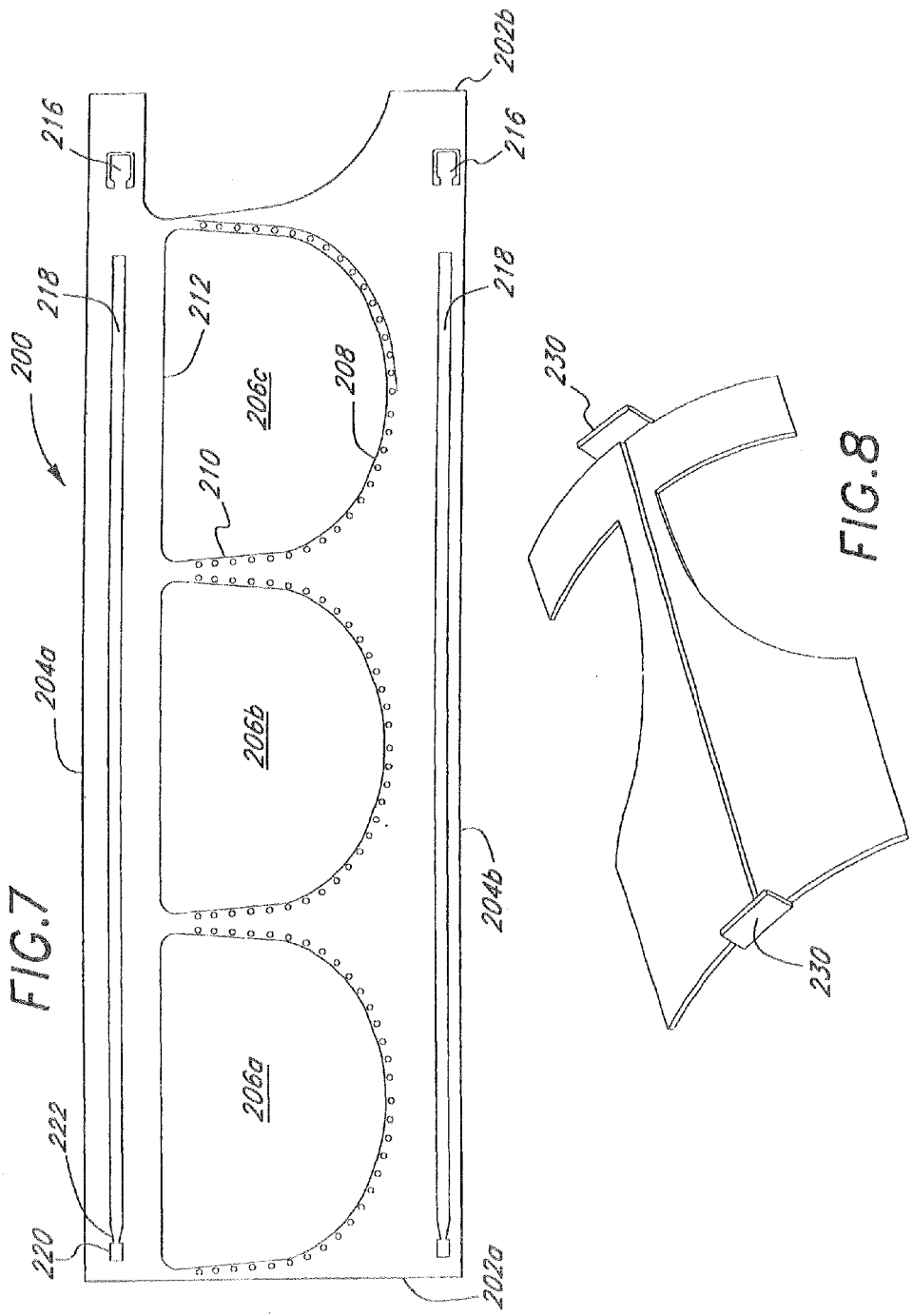

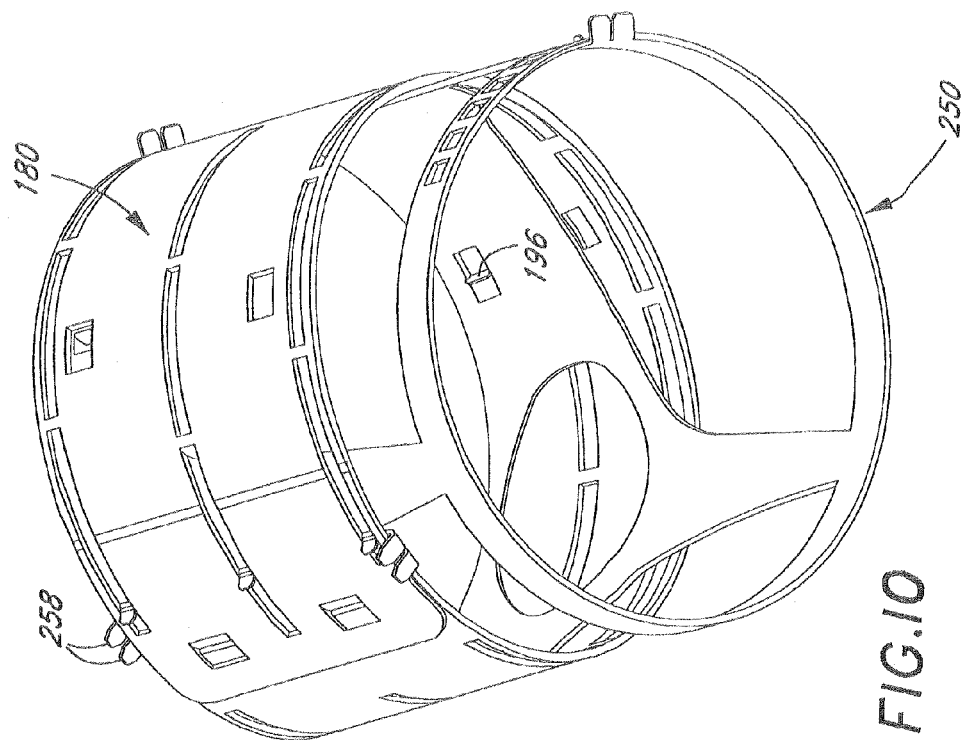
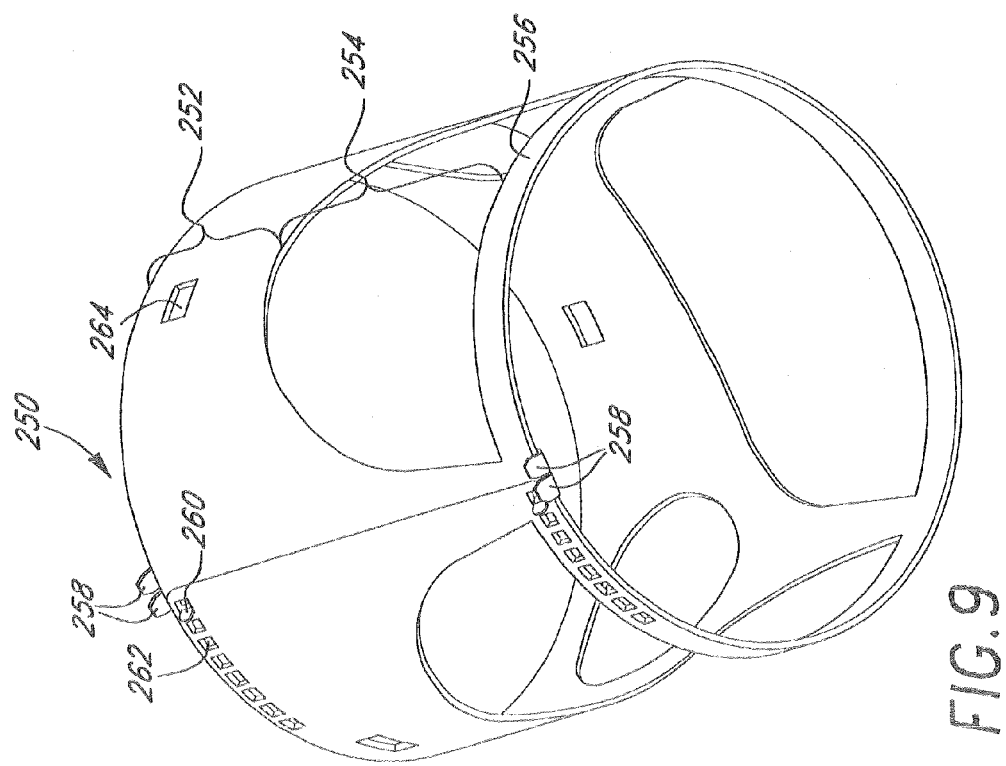

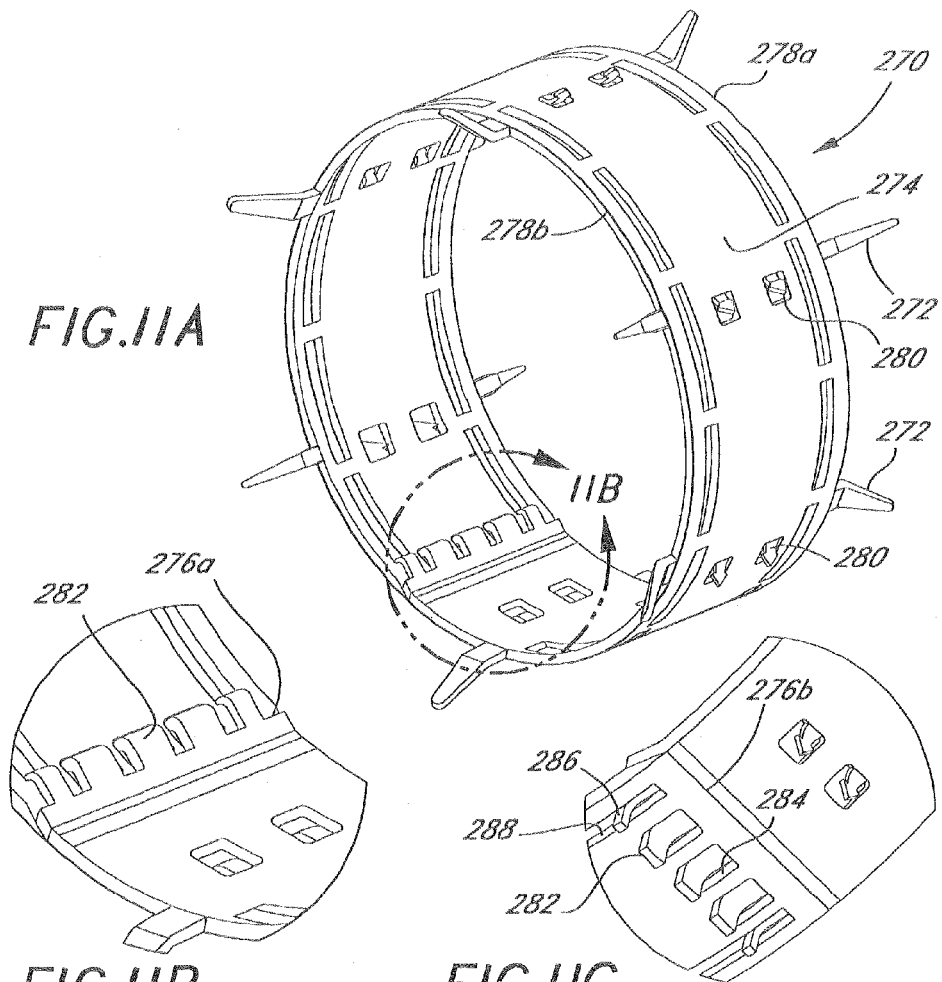
FIG.11A
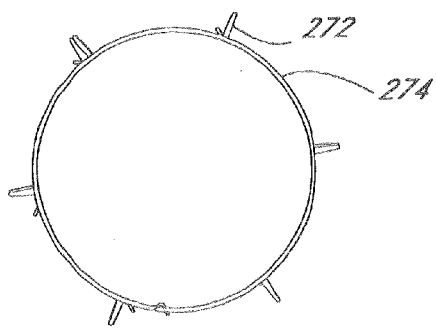
FIG.11B
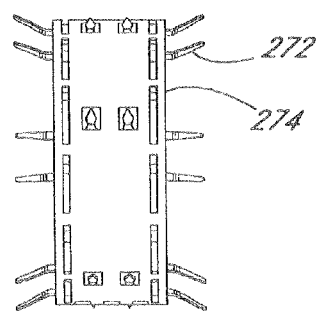
FIG.11C
FIG.11D
FIG.11E

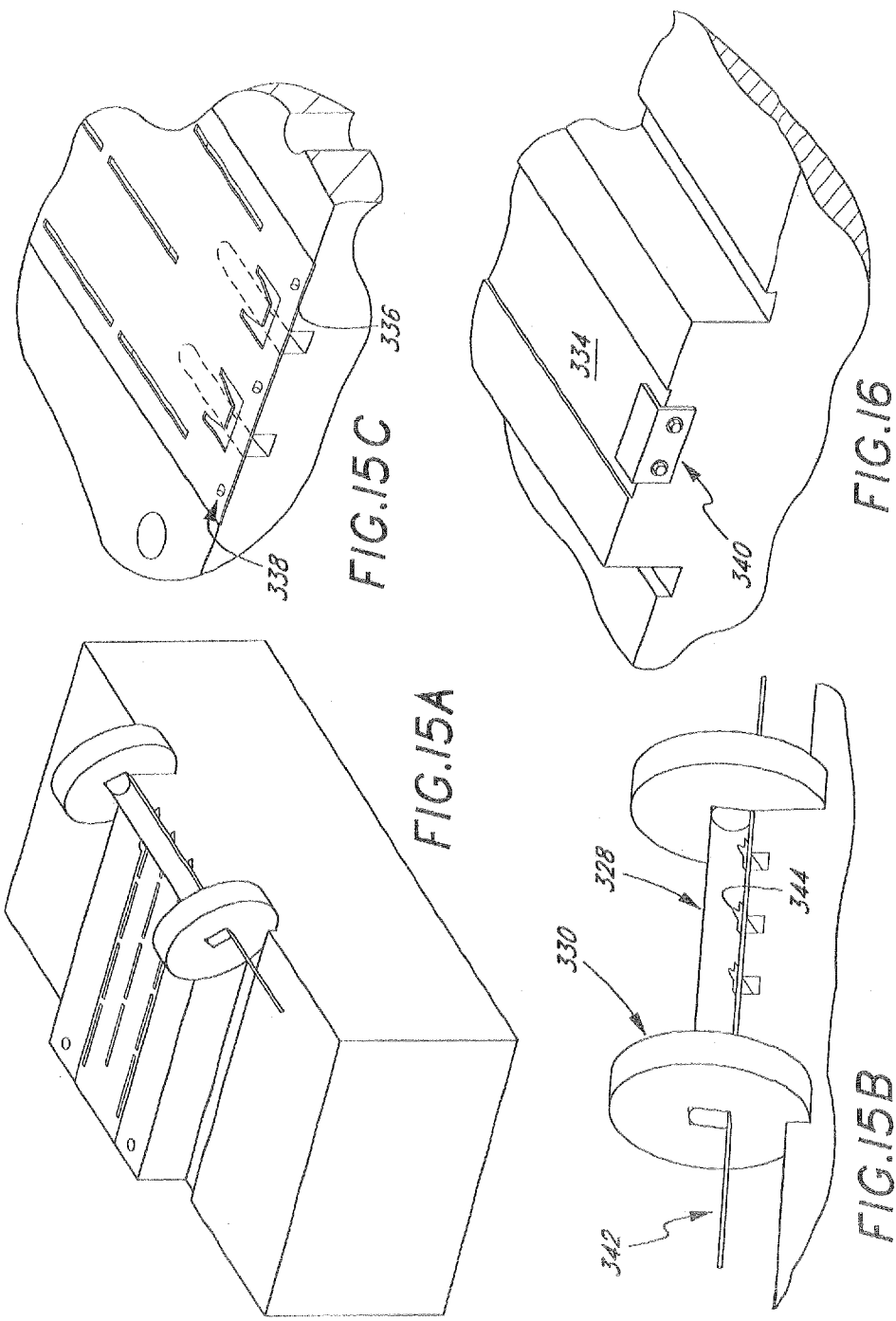

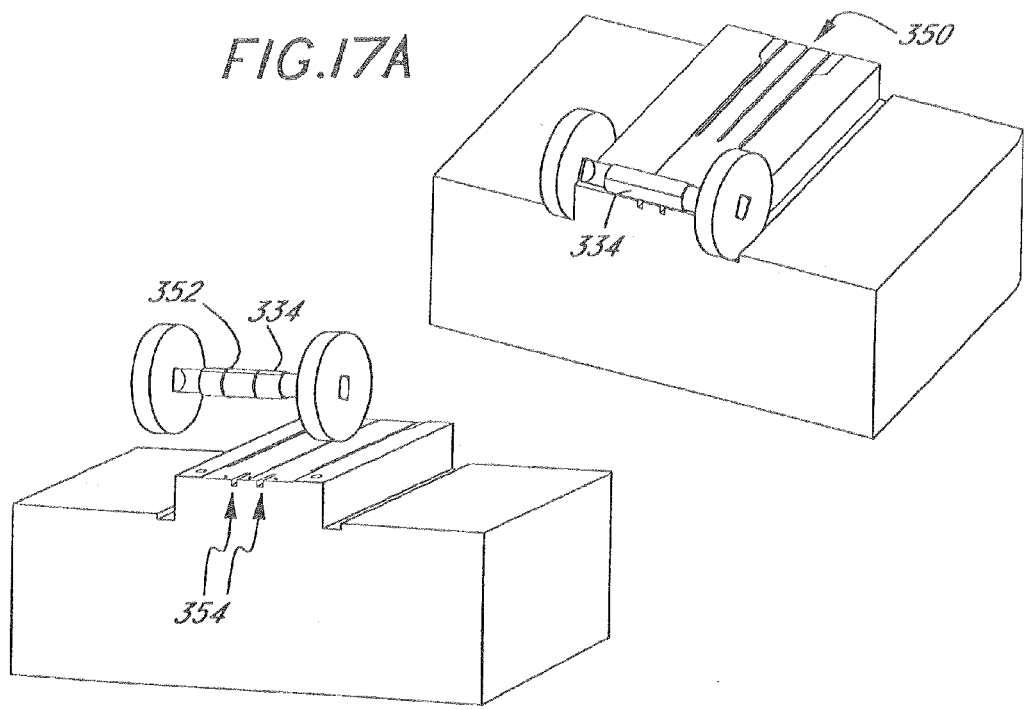
FIG.17A
FIG.17B
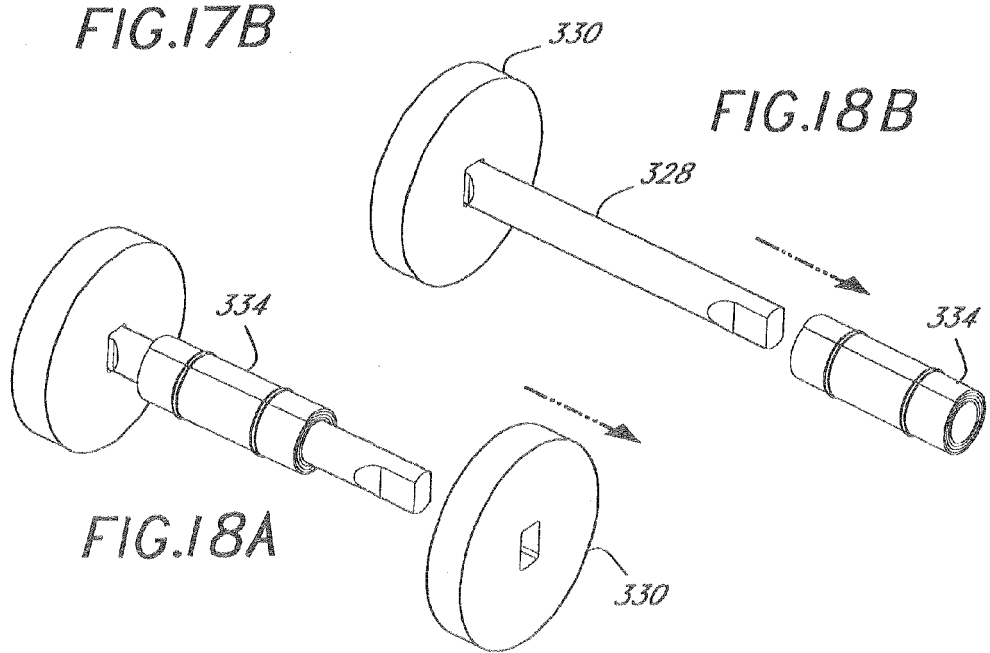
FIG.18B
FIG.18A

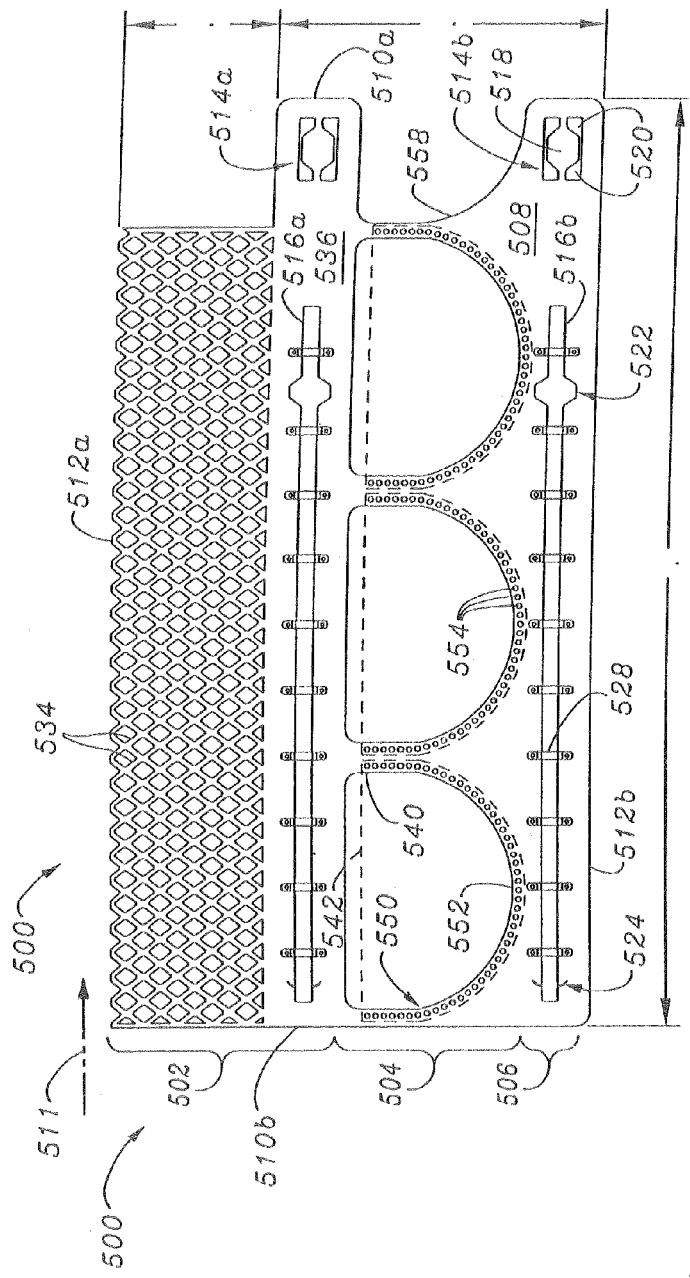
Fig. 20A
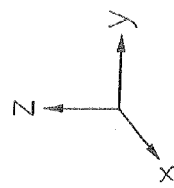
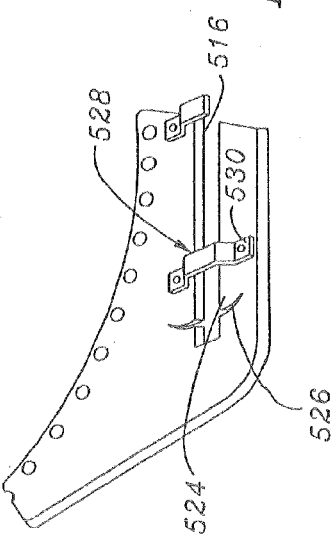
Fig. 20B

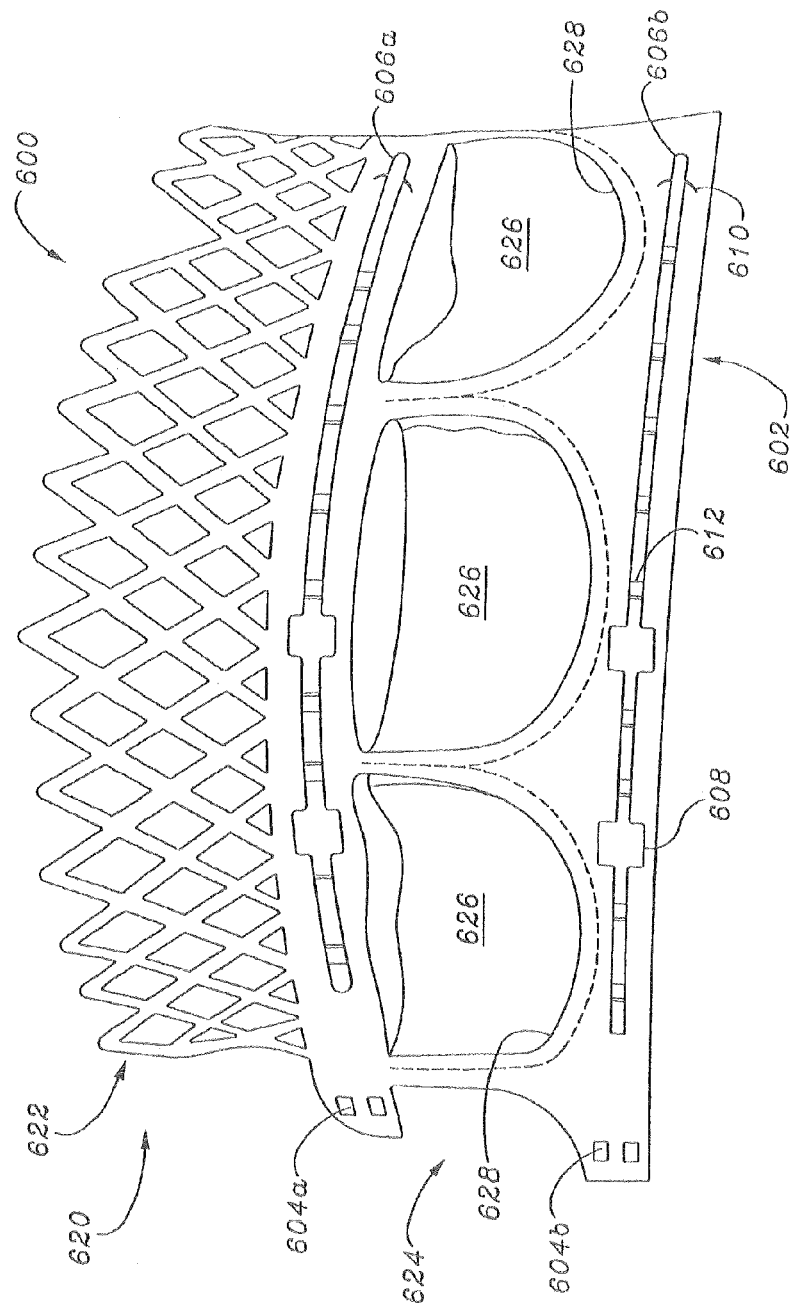

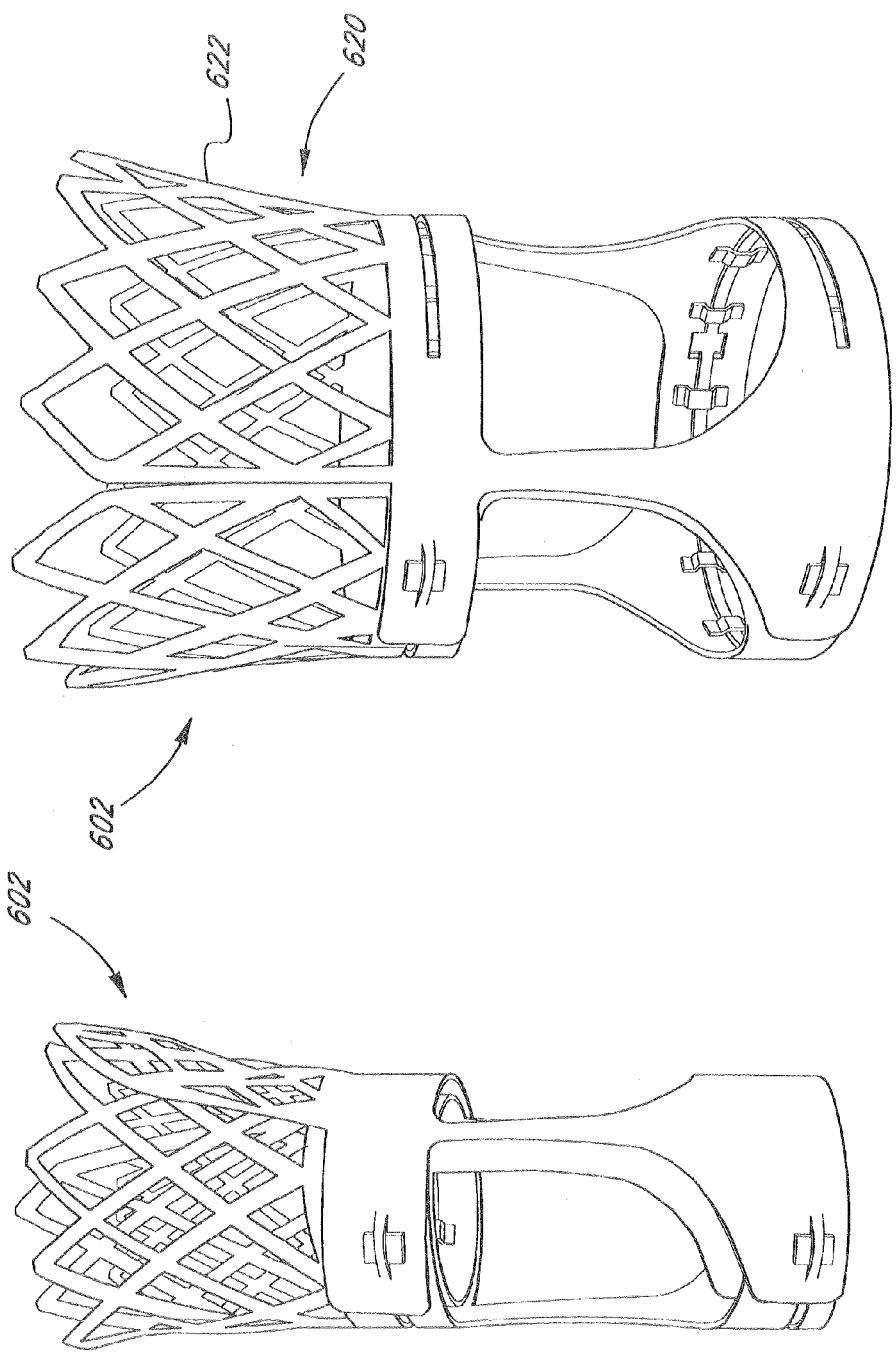

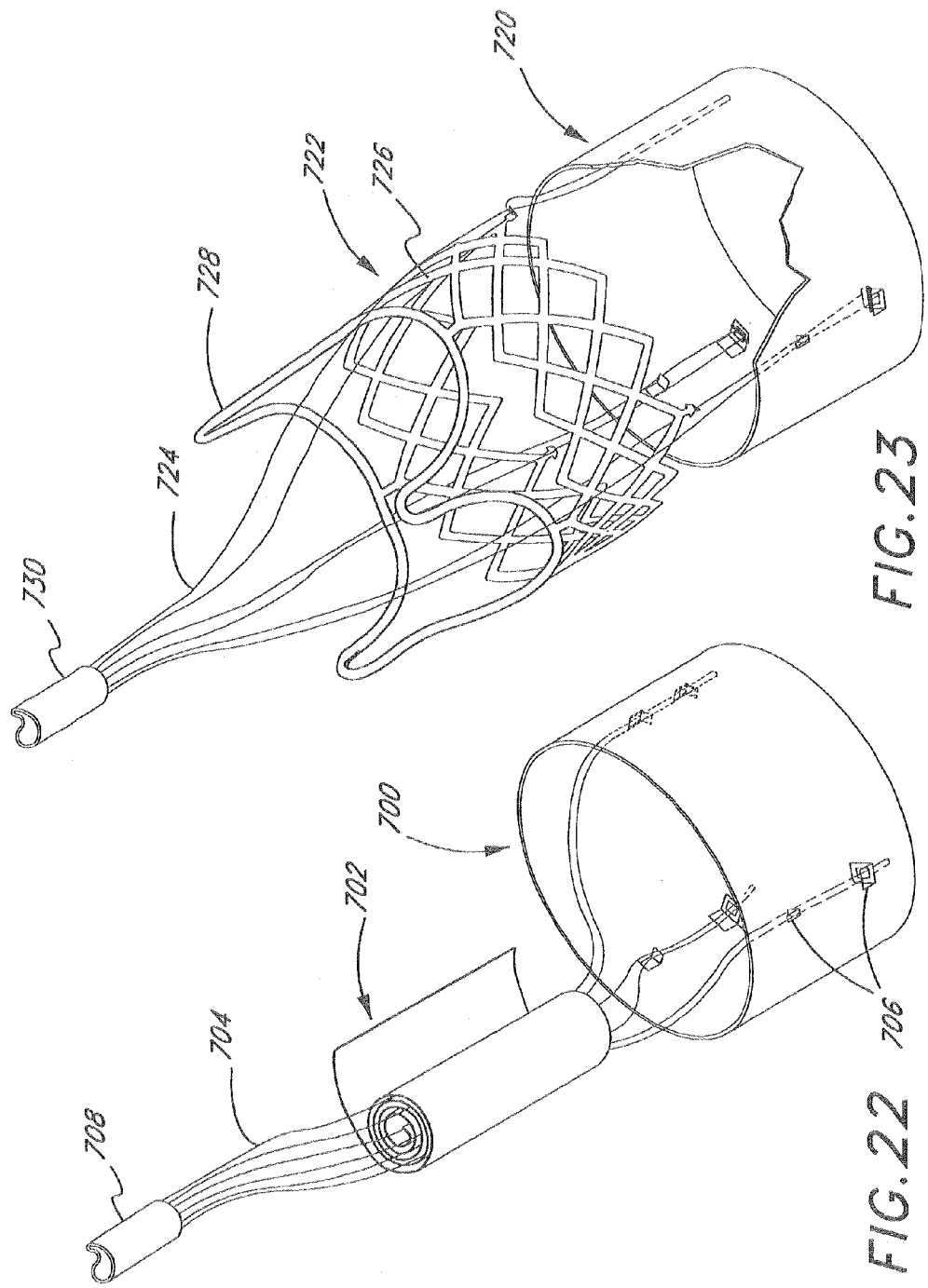

TWO-PART EXPANDABLE HEART VALVE

RELATED APPLICATIONS

The present application is a continuation of Ser. No. 10/653,843, now U.S. Pat. No. 7,276,084, filed Sep. 2, 2003, which is a continuation of Ser. No. 09/815,521, now U.S. Pat. No. 6,733,525, filed Mar. 23, 2001.

FIELD OF THE INVENTION

The present invention relates generally to medical devices and particularly to expandable heart valve prostheses especially for use in minimally-invasive surgeries.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment. Importantly, the wireform provides continuous support for each leaflet along the cusp region so as to better simulate the natural support structure.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Some attempts have been made to enable less traumatic delivery and implantation of prosthetic heart valves. For instance, U.S. Pat. No. 4,056,854 to Boretos discloses a radially collapsible heart valve secured to a circular spring stent that can be compressed for delivery and expanded for securing in a valve position. Also, U.S. Pat. No. 4,994,077 to Dobbin describes a disk-shaped heart valve that is connected to a radially collapsible stent for minimally invasive implantation.

Recently, a great amount of research has been done to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still typically requires bypass, but the excision of the native valve and implantation of the prosthetic valve are accomplished via elongated tubes or cannulas, with the help of endoscopes and other such visualization techniques.

Some examples of more recent MIS heart valves are shown in U.S. Pat. No. 5,411,552 to Anderson, et al., U.S. Pat. No. 5,980,570 to Simpson, U.S. Pat. No. 5,984,959 to Robertson, et al., PCT Publication No. 00/047139 to Garrison, et al., and PCT Publication No. WO 99/334142 to Vesely. Although these and other such devices provide various ways for collapsing, delivering, and then expanding a "heart valve" per se, none of them disclose an optimum structure for tissue valves. For instance, the publication to Vesely shows a tissue leaflet structure of the prior art in FIG. 1, and an expandable inner frame of the invention having stent posts in FIGS. 3A-3C. The leaflets are "mounted to the stent posts 22 in a manner similar to that shown in FIG. 1." Such general disclosures as in Vesely stop short of explaining how to construct a valve in a manner that maximizes long-term efficacy. In particular, the means of attaching the leaflets to the MIS stent is critical to ensure the integrity and durability of the valve once implanted. All of the prior art MIS valves are inadequate in this regard.

Another problem with MIS valves of the prior art is their relatively large radial dimension during implantation. That is, these valves all utilize one or more radially-expanding stents coupled to a biological valve, and the assembly must be compressed radially and then passed through the lumen of a large bore catheter. Reducing the radial profile of the constricted valve via radial compression is problematic and conflicts with the need for sufficient circumferential length of the valve in its expanded state to fit within an adult heart valve annulus. Moreover, radial compression of the stent and biological valve must be done with great care so as not to damage the valve.

Some MIS valves of the prior art are intended to be used without removing the natural valve leaflets. Sometimes the natural leaflets are heavily calcified, and their removal entails some risk of plaque particles being released in the bloodstream. Therefore some of the MIS valves are designed to expand outward within the annulus and native leaflets, and compress the leaflets against the annulus. In doing so, a relatively uneven surface against which the valve is expanded outward is created. This irregularity creates sizing problems, and also may adversely affect the circularity of the expanded valve which negatively affects the valve efficacy by impairing leaflet coaptation.

Despite some advances in MIS valve design, there remains a need for a valve that can be constricted into a smaller package without damaging the biological valve within, and which can be reliably expanded generally into a tube against the relatively uneven surface of the annulus or annulus and intact native leaflets.

SUMMARY OF THE INVENTION

The present invention provides an expandable prosthetic heart valve for placement in a host heart valve annulus, comprising a stent body that is rolled into a compact configuration, implanted, then unrolled into a tubular shape and secured into place in the valve annulus. The valve is small enough in its contracted state to be passed down a delivery tube, thus avoiding the need for open heart surgery. Flexible membranes attach around large apertures in the inner wall of the stent body and have sufficient play to billow inward into contact with one another and form the one-way valve occluding surfaces. The stent may be one or two pieces, and the delivery and implantation may occur in one or two steps using one or two delivery tubes.

In a preferred embodiment, a prosthetic heart valve of the present invention suitable for minimally invasive delivery comprises a generally sheet-like stent body and a plurality of flexible, biocompatible membranes incorporated into the stent body to form heart valve leaflets. The stent body has a first, contracted configuration in which it is spirally-wound about an axis such that at least one winding of the stent body surrounds another winding. The stent body further has a second, expanded configuration in which it is substantially unwound and at least partly forms a tube centered about the axis and sized to engage an annulus of a patient's heart valve. In accordance with one aspect, the stent body comprises a primary stent coupled to a secondary stent that at least partially fits within the primary stent. The flexible, biocompatible membranes are incorporated into the secondary stent. Alternatively, the stent body is formed of a single stent.

The stent body may have a plurality of sinus apertures with an outer edge of each biocompatible membrane fastening around the edge of an aperture. The sinus apertures may be generally semi-circular or generally oval. The outer edge of each membrane is desirably folded over to contact an inner surface of the stent body adjacent an edge of the associated aperture.

One embodiment of a heart valve of the present invention includes at least one guide to insure concentricity of the sheet-like stent body about the axis during a conversion between the first, contracted configuration to the second, expanded configuration. For example, the stent body may define a pair of opposed side edges that generally mate in the second, expanded configuration, and a pair of opposed end edges that extend between the side edges, and the at least one guide comprises a tab extending generally radially along each one of the end edges. Alternatively, the at least one guide comprises a tab extending generally radially from the stent body and a cooperating slot in the stent body circumferentially spaced from and axially aligned with the tab. In the latter case, the tab enters and is retained within the slot during the conversion between the first, contracted configuration to the second, expanded configuration.

In a further aspect of the present invention, the stent body defines a pair of opposed side edges that generally mate in the second, expanded configuration, and the stent body further includes lockout structure to retain the opposed side edges in mating engagement. The lockout structure may comprises tabs formed adjacent one of the side edges and apertures formed adjacent the other of the side edges that are sized to receive and retain the tabs. Desirably, the lockout structure both prevents further expansion of the stent body and contraction from the expanded tubular shape.

At least one anchoring barb may be provided extending radially outward from the stent body in the second, expanded configuration. Where the stent body defines a pair of opposed side edges that generally mate in the second, expanded configuration, and a pair of opposed end edges that extend between the side edges, the anchoring barb extends from one of the end edges.

Preferably, the stent body is formed of a single stent having an anchoring section on an inflow end, a sinus section, and an outflow section. The sinus section is between the anchoring section and outflow section, and has apertures for receiving flexible biocompatible membranes that form the occluding surfaces of the valve. Each biocompatible membrane fastens around the edge of an aperture, wherein the sinus apertures may be generally semi-circular and the outer edge of each membrane is folded over to contact an inner surface of the stent body adjacent an edge of an aperture. The outflow section may flare outward from the sinus section, and may include an apertured lattice, mesh or grid pattern.

The present invention further provides a method of prosthetic heart valve implantation, comprising providing a prosthetic heart valve in a spirally-wound contracted configuration, delivering the prosthetic heart valve in its contracted configuration through a delivery tube to a heart valve annulus, and unfurling the prosthetic heart valve from its contracted configuration to an expanded configuration that engages the heart valve annulus.

The prosthetic heart valve may comprise a single stent body having a plurality of flexible, biocompatible membranes incorporated therein that form heart valve leaflets in the expanded configuration. Alternatively, the prosthetic heart valve comprises a two-piece stent body with a primary stent and a secondary stent, wherein the steps of delivering and unfurling comprise delivering and unfurling the primary stent first and then delivering and unfurling the secondary stent within the primary stent. The secondary stent may be guided into coupling position within the primary stent using one or more guidewires. The method further may include anchoring the prosthetic heart valve in its expanded configuration to the heart valve annulus. If the native heart valve leaflets of the heart valve annulus are left in place, the step of unfurling causes the prosthetic heart valve to contact and outwardly compress the native leaflets. The step of unfurling further may include ensuring that the prosthetic heart valve remains generally concentric about a single axis, and also locking the prosthetic heart valve in its expanded configuration.

A further understanding of the nature and advantages of the invention will become apparent by reference to the remaining portions of the specification and drawings.

BRIEF DESCRIPTION OF THE DRAWINGS

FIG. 1 is a perspective view of an exemplary one-piece expandable heart valve stent of the present invention;

FIG. 2A is a perspective view of an exemplary expandable heart valve of the present invention utilizing the stent of FIG. 1;

FIG. 2B is a cross-sectional view taken along line 2B-2B through one side of the heart valve of FIG. 2A showing a preferred leaflet attachment construction;

FIG. 2C is a perspective view of an alternative one-piece expandable heart valve stent of the present invention having a flared outflow end;

FIG. 3A is a perspective view of an exemplary two-piece expandable heart valve stent of the present invention having oval-shaped sinus apertures and leaflet attachment strips;

FIGS. 3B and 3C are end and side elevational views of the heart valve stent of FIG. 3A;

FIGS. 4A and 4B are alternative perspective views of an exemplary primary stent for use in an expandable heart valve of the present invention, particularly illustrating side tabs for alignment during unrolling;

FIGS. 5A and 5B are alternative partial perspective views of a further primary stent for use in an expandable heart valve of the present invention, particularly illustrating body tabs and slots for alignment during unrolling;

FIGS. 6A-6D are different perspective views of a further primary stent for use in an expandable heart valve of the present invention;

FIG. 7 is a plan view of an exemplary secondary stent for use in an expandable heart valve of the present invention, particularly illustrating generally semicircular sinus apertures circumscribed by leaflet attachment holes, and body tabs and slots for alignment during unrolling;

FIG. 8 is a partial perspective view of a commissure/junction region of an exemplary secondary stent, particularly illustrating side tabs for alignment during unrolling;

FIG. 9 is a perspective view of an exemplary expanded secondary stent of the present invention;

FIG. 10 is a perspective view of a primary stent like that shown in FIG. 6A coupled to a secondary stent like that shown in FIG. 10;

FIGS. 11A-11C are different perspective views of a further exemplary primary stent having both edge and body barbs for use in an expandable heart valve of present invention;

FIGS. 11D and 11E are end and side elevational views of the heart valve stent of FIG. 11A;

FIGS. 15A-15C are perspective views of the exemplary stent rolling apparatus illustrating details of first and second side edges of the stent;

FIG. 16 is a perspective view of an alternative means for securing a second edge of a stent being rolled;

FIGS. 17A and 17B are schematic perspective views of a stent after having been rolled in accordance with the present invention;

FIGS. 18A and 18B are schematic perspective views of a rolled stent being removed from a rolling mandrel;

FIG. 20A is a plan view of another one-piece expandable heart valve stent of the present invention having a flared cage-like outflow section;

FIG. 20B is a detailed perspective view of one end of a guide slot in the heart valve stent of FIG. 20A;

FIG. 21A is a plan view of a heart valve having a one-piece expandable stent similar to that shown in FIG. 20A in several configurations from FIGS. 21B and 21C are perspective views of the one-piece expandable heart stent of FIG. 21A in partially and fully unrolled configurations, respectively;

FIG. 22 is a schematic perspective view of a two-piece heart valve stent assembly prior to coupling a secondary stent to a primary stent using guidewires; and FIG. 23 is a schematic perspective view of a two-piece heart valve stent assembly prior to coupling a secondary stent having a wireform structure to a primary stent using guidewires.

DESCRIPTION OF THE PREFERRED EMBODIMENTS

Figure 12:
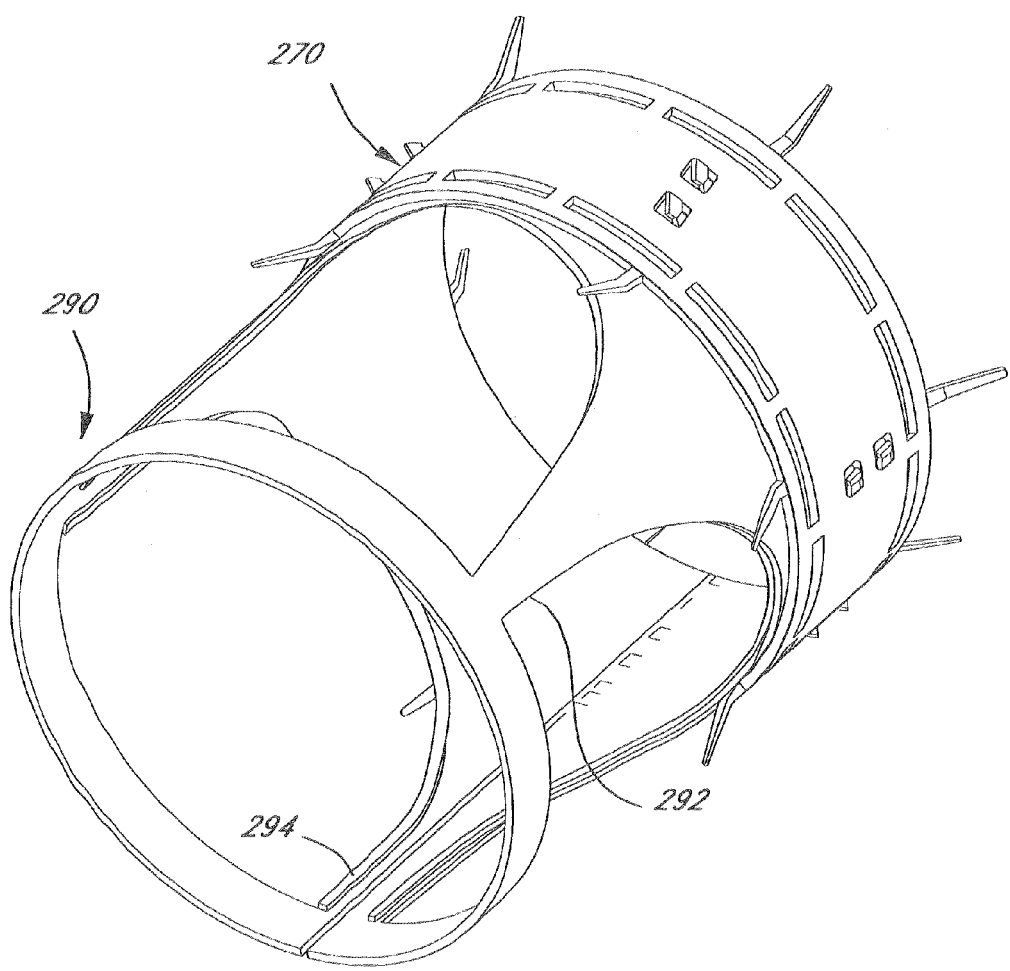
FIG. 12 is a perspective view of a secondary stent coupled to a primary stent like that shown in FIG. 11A.

The present invention discloses a number of expandable heart valves for implantation in a host annulus, or host tissue adjacent the annulus. The valves may be implanted in any of the four valve positions within the heart, but are more likely to be used in replacing the aortic or mitral valves because of the more frequent need for such surgery in these positions. The patient may be placed on cardiopulmonary bypass or not, depending on the needs of the patient.

A number of expandable prosthetic heart valves are disclosed that are initially rolled into a tight spiral to be passed through a catheter or other tube and then unfurled or unrolled at the implantation site, typically a valve annulus. The heart valves comprise one- or two-piece stent bodies with a plurality of leaflet-forming membranes incorporated therein. Various materials are suitable for the stent body, although certain nickel-titanium alloys are preferred for their super-elasticity and biocompatibility. Likewise, various materials may be used as the membranes, including biological tissue such as bovine pericardium or synthetic materials. It should also be noted that specific stent body configurations disclosed herein are not to be considered limiting, and various construction details may be modified within the scope of the invention. For example, the number and configuration of lockout tabs (to be described below) may be varied.

Those of skill in the art will recognize that the means and techniques for delivering and implanting the prosthetic heart valves disclosed herein are numerous and not the specific focus of the present application. In general, the heart valves in a first, contracted configuration are delivered through a tube such as a percutaneously-placed catheter or shorter chest cannula and expelled from the end of the tube in the approximate implantation location. The heart valve is then expanded via a balloon, mechanical means, or self-expanded from internal elastic forces, into a second, expanded configuration that engages the native host tissue, such as the target valve annulus. Depending on the native valve being replaced, the prosthetic heart valve may have varying axial lengths. For example, in the aortic position, a portion of the valve may extend upward into and even contact the aorta to better stabilize the commissure regions of the valve. In other words, the particular design of the valve may depend on the target valve location.

With reference to FIGS. 1 and 2A-2B, an exemplary one-piece prosthetic heart valve 20 (complete in FIG. 2A) of the present invention is shown. The valve 20 comprises a stent body 22 that is shown isolated in FIG. 1, and a plurality of leaflet-forming membranes 24. The stent body 22 is shown in both FIGS. 1 and 2A in its expanded configuration generally defining a tube centered about an axis. The membranes 24 fasten within the stent body 22 so as to form a one-way valve therewithin, and orient the valve to have an inflow end 28 and an outflow end 30. In a preferred embodiment, there are three such membranes 24 each having a free edge 32 that extends inward from the stent body 22 and coapts or meets the other two free edges generally along radial lines spaced apart 120° with respect to each other to close the valve during the back flow cycle of blood flow, as seen in FIG. 2A. When blood flows in the opposite direction, from the inflow to the outflow end, the free edges 32 of the membranes 24 move radially outward away from each other to open the valve.

With specific reference to FIG. 1, the tubular stent body 22 comprises three sections, starting at the inflow end 28 and moving toward the outflow end 30: an annulus anchoring section 40, a sinus section 42, and an outflow section 44. The three sections 40, 42, and 44 are desirably formed from a single generally sheet-like piece of material that can be cohesively rolled into a tight spiral and expanded into the tubular configuration shown. In this regard, the stent body 22 includes an axially-oriented first side edge 50 that mates with an axially-oriented second side edge 52 along longitudinal seam 53. The two side edges 50, 52 abut or overlap and lock together using one or more, preferably two or more cooperating tabs 54 and slots 56. In the illustrated example, two series of slots 56a, 56b are provided around the circumference of the stent body 22 adjacent the first side edge 50, while a pair of engaging tabs 54a, 54b are provided adjacent the second side edge 52.

The annulus anchoring section 40 is desirably substantially solid and free of perforations so as to more reliably retain its tubular shape upon outward expansion against the native heart valve annulus. In a preferred implantation technique, the prosthetic heart valve 20 expands outward and compresses against the native leaflets which present a relatively uneven base. Even if the leaflets are excised, the circularity of the annulus depends on the skill of the surgeon. Minimizing any openings in the anchoring section 40 enhances its rigidity so as to ensure a relatively tubular support structure for the leaflet-forming membranes 24. However, anchoring barbs 60 may be provided in the anchoring section 40, and may be formed by integrally cut tabs as shown. In addition, a pair of openings 62 may be optionally provided in the side wall of the tubular stent body 22 to reduce the roll-up stiffness.

With reference to FIG. 2A, the sinus section 42 comprises a plurality (preferably three) of generally axially extending commissures 70 and curvilinear cusps 72 defined by relatively large sinus apertures 74 in the stent body 22. In the illustrated embodiment, the sinus apertures 74 are generally semi-circular with a straight, circumferential edge 76 defined by the beginning of the outflow section 44. A plurality of small attachment apertures 78 track along the edge of the sinus apertures 74, extending around the curvilinear cusps 72 and substantially up the entire commissures 70.

The membranes 24 fasten to the stent body 22 using the attachment apertures 78. More particularly, as seen in FIG. 2B, an outer edge portion 80 of each membrane 24 folds upward in the outflow direction to lie against an inner surface 84 of the stent body 22. This folded attachment helps reduce localized stresses caused by the sutures through the membrane 24, and enhances coaptation of the free edges 32 at the commissures 70. Fasteners such as sutures 82 secure the outer edge portion 80 flush against the inner surface 84. The sutures typically loop through the membrane 24 twice at each attachment aperture 78 in a single mattress stitch, though various other stitching techniques are known. In a preferred embodiment, the attachment apertures 78 are spaced apart a minimum distance of about 0.004-0.0075 inches for strength.

A small lip 86 of the outer edge portion 80 desirably projects beyond the sinus aperture 74 to help protect the membrane 24 from rubbing directly against the material of the stent body 22 during operation of the valve. That is, there is membrane-to-membrane cushioned contact at the sinus apertures 74 when the membranes 24 are forced outward in the opening cycle of the valve.

Additionally, all exposed edges of the stent body 22 are electropolished or coated with a layer of lubricious material (e.g., PTFE or "TEFLON") to eliminate any sharp corners and thus reduce wear on the flexible membranes 24.

The free edge 32 of each membrane 24 meets the stent body 22 at one of the commissures 70. Because adjacent arrays of attachment apertures 78 converge in the outflow direction along each commissures 70, the free edges 32 of adjacent membranes 24 coapt at or closely adjacent to the stent body inner surface 84, as best seen in FIG. 2A. This configuration eliminates leakage between the free edges 32 when the valve closes.

The outflow section 44 desirably comprises at least a circular band 90 of material that joins the outflow ends of the commissures 70. In the illustrated embodiment, the outflow section 44 further includes a second band 92 axially spaced from the first band 90 and joined thereto with a lattice, mesh or grid 94. The outflow section 44 may not be in contact with any tissue of the heart, but rather project into the respective outflow chamber as a support for the three commissures 70. That is, substantial inward radial loads are imposed on the commissures 70 during the closing cycle of the valve, and the outflow section 44 maintains the spacing between the commissures to ensure proper coaptation of the membrane free edges 32. The grid 94 defines more spaces than connecting struts, and thus minimizes interference with proper blood flows in the outflow chamber. The outflow section 44 may be rigid, or may be somewhat flexible to mirror aortic wall movement.

In FIG. 2C, an alternative stent body 22' has a flared outflow section 44' section that conforms to and contacts the aortic wall in an aortic valve replacement setting. The aortic wall and sinuses diverge outward from the annulus, in which the annulus anchoring section 40' resides. Therefore, the outward flaring of the outflow section 44' permits contact with the aortic wall and better stabilizes the valve in its implantation position. Further, the backflow volume on the outflow side of the leaflets will be slightly increased which may enhance valve closing. The outflow section 44' may be formed to spring open to the flared shape, or may be plastically deformed into the flared shape using a non-cylindrical expansion balloon. For example, the outflow section 44' may be annealed Nitinol that self-expands to the flared shape upon being released from within a delivery tube. Further embodiments of stents having the flared outflow section are shown and described below.

With reference to FIGS. 3A-3C, an exemplary two-piece stent body 100 comprises a generally ring-shaped primary stent 102 and a tubular secondary stent 104 coupled therewithin. The primary stent 102 is shown isolated in FIGS. 4A and 4B and includes a first side edge 106, a second side edge 108, and a pair of opposed end edges 110a, 110b. A pair of alignment tabs 112 projects radially outward from the end edges 110a, 110b adjacent the second side edge 108. The alignment tabs 112 provide guides for use during unfurling of the primary stent 102 to maintain concentricity about a central axis. That is, as the primary stent 102 transitions between a first, contracted configuration (i.e., a tight spiral) and a second, expanded configuration, the alignment tabs 112 prevent the stent from unrolling to form a cone. Desirably, in the first, contracted configuration, the primary stent 102 is spirally-wound about an axis such that at least one winding of the stent body 100 surrounds another winding, and preferably there are numerous windings to reduce the radial profile of the stent 102. Desirably, the second side edge 108 resides at the center of the tightly rolled second configuration such that as the stent 102 unrolls, the end edges 110a, 110b slide by and are constrained within the tabs 112. In addition, the primary stent 102 includes lockout structure in the form of a pair of tabs 114 projecting radially inward near the first side edge 106 and a pair of notches 116 in the second side edge 108. The tabs 114 fit within the notches 116 and lock the two side edges 106, 108 together. Desirably, a bi-directional locking arrangement is provided to prevent contraction of the stent but also further expansion. There are preferably two locking tabs/slots along the mating edges, desirably located symmetrically about an axial midplane of the stent.

Referring to FIGS. 3A-3C, the secondary stent 104 includes a generally solid inflow section 120, a sinus section 122, and an outflow band 124. The sinus section 122 is relatively more solid than the sinus section 42 of the first embodiment, and includes a plurality, preferably three, oval-shaped sinus apertures 126. A leaflet-forming membrane (not shown)

fastens around the inflow edge of each of the sinus apertures 126 in such a manner so as to coapt within the tubular stent body 100 and define the valve occluding surfaces. More specifically, a membrane fastening strip 128 follows the edge contour of each membrane with a pair of commissure regions 130 and a curvilinear cusp region 132 and provides an anchor to which the membrane may be attached. The fastening strip 128 may be made of pericardium, and may be fastened to the inner surface of the secondary stent 104 using stitching or other suitable expedient.

In an exemplary embodiment, secondary stent 104 includes at least one locking tab 140 that projects outwardly through a locking window 142 in the primary stent 102 to retain the two stents in cooperating relationship. The secondary stent 104 includes a first side edge 144 and a second side edge 146 that overlap and are locked together using suitable tabs/notches (not further described herein). In use, the primary stent 102 is first delivered and then unfurled and secured in the native annulus, after which the secondary stent 104 is delivered and then unfurled and locked within the primary stent. One or more alignment tabs 150 may be provided on the secondary stent 104 to engage alignment slots 152 and ensure the secondary stent unfurls concentrically around the axis. Furthers the outwardly projecting alignment tabs 112 and locking tab(s) 140 may double as anchoring barbs projecting into the native tissue.

Alternatively, a ratchet type of locking arrangement can be provided for the primary stent 102 or secondary stent 104 to enable greater size adjustment. For instance, multiple engaging teeth may be formed on either stent 102 or 104 to enable substantially continuous size adjustment beyond a minimum annulus diameter. The ratchet teeth may be on circumferentially opposed surfaces or a bent end tab may engage teeth provided on a circumferential edge of the stent. Likewise, coupling structure between the primary and secondary stents may be used other than the tabs/slots shown. For instance, a hook and loop connection may be realized by expanding the secondary stent within the primary stent.

FIGS. 5A and 5B show in greater detail exemplary alignment tabs/slots and locking tabs/notches. These figures illustrate an exemplary primary stent having a first side edge 160 and a second side edge 162, although the same concepts may be applied to a secondary stent. A pair of alignment tabs 164 projects radially outward from the second side edge 162 and a second pair of alignment tabs 166 projects radially outward from the body of the stent. A series of circumferential slots 168 are provided along the length of the stent such that the tabs 164, 166 are received therein during the unfurling process. The slots 168 guide the tabs 164, 166 to prevent the stent from unfurling into a cone. Once the stent has fully expanded, a pair of locking tabs 170 projecting radially inward from near the first side edge 160 engages a pair of notches 172 in the second side edge 162.

FIGS. 6A-6D illustrate a still further primary stent 180 that is similar to, but slightly axially longer than, the primary stent 102 described above. Again, the stent 180 includes overlapping first and second side edges 182a, 182b, respectively, and circumferentially disposed end edges 184a, 184b. As seen best in FIGS. 6B and 6C, three alignment tabs 186 project radially outward from the second side edge 182b into alignment slots 188. As before, these alignment tabs and slots prevent the primary stent 180 from unfurling unevenly to form a cone. It should be noted that the middle alignment slot 188 is circumferentially staggered with respect to the two alignment slots near the end edges 184a, 184b such that at least one alignment tab 186 resides in one of the slots at all times. Additionally, two pairs of alignment tabs 190 project radially outward from the end edges 184a, 184b at the second side edge 182b, further insuring against misalignment during the unfurling process. A pair of locking tabs 192 projects inward from the primary stent 102 near the first side edge 182a and engages a cooperating pair of locking notches 194 formed in the second side edge 182b. As can be appreciated from FIG. 6B, the locking tabs 192 and notches 194 prevent the primary stent 180 from contracting once it has been fully expanded. Finally, FIG. 6D is a detail of an inwardly directed coupling tab 196 that may be used to couple a secondary stent to the primary stent 180. In the illustrate embodiment, there are three such coupling tabs 196 distributed evenly about the stent.

FIG. 7 illustrates a secondary stent 200 of the present invention in plan view, before being rolled into its contracted configuration. The stent 200 has a generally rectangular periphery defined by a first side edge 202a, a second side edge 202b, and a pair of linear end edges 204a, 204b. Again, the secondary stent 200 comprises a generally sheetlike body that can be rolled into a relatively tight configuration and unrolled into a tube. Three sinus apertures 206a, 206b, 206c formed in the secondary stent 200 each having a curvilinear cusp 208 and a pair of generally linear commissures 210 of either side of the cusp. The commissures 210 are joined by an outflow band 212. A pair of combined alignment and locking tabs 216 is sized to translate within respective alignment slots 218 to insure even unfurling of stent 200. A pair of locking notches 220 is formed at the end of the alignment slots 218 closest to the first side edge 202a. The locking tabs 216 have an enlarged head joined by a neck to the body of the stent 200 and the locking notches 220 also include a tapered neck 222 that permits passage of the tab neck in only one direction so as to lock it therein.

FIG. 8 is a detailed isolation of overlapping side edges of a secondary stent showing alignment tabs 230 disposed on side edges of the inner layer of the stent. These alignment tabs 230 therefore can replace the alignment tabs 216 and slots 218 of the secondary stent 200 of FIG. 7, although alternative locking structure must be provided.

FIG. 9 illustrates a still further secondary stent 250 of the present invention, and FIG. 10 illustrates the same stent coupled with the primary stent 180 of FIG. 6A. The secondary stent 250 includes many of the same features described above, including a generally solid inflow section 252, a sinus section 254, and an outflow band 256 (again, the leaflet-forming membranes are not shown to better illustrate the stent). The body of the stent 250 includes two pairs of side alignment tabs 258 that prevent the stent 250 from unfurling into a conical form. One or more lockout tabs 260 extend outward from one side edge of the stent 250 and engage one or more apertures 262 in the other side edge to secure the edges in an overlapping relationship as shown. A plurality of coupling windows 264 is located at evenly-spaced circumferential intervals around the body of the stent 250 to receive and retain coupling tabs 196 extending inward from the primary stent 180 (see FIG. 6D). Note in FIG. 10 that the alignment tabs 258 closely conform to the inflow end of the primary stent 180 and further help retain the stent assembly together. Also, these alignment tabs 258 may serve as anchoring barbs to retain the valve in the host annulus.

FIGS. 11A-11E illustrate another primary stent 270 that features a plurality (at least three) of outwardly angled anchoring spikes 272. The stent 270 includes a band-like body 274 having a first side edge 276a and a second side edge 276b, with opposed and parallel end edges 278a, 278b extending therebetween. The anchoring spikes 272 extend axially away and then radially outward from the respective end edges 278a, 278b a distance of between about 1-2 mm. There are desirably at least three anchoring spikes 272 extending from each end edge 278a, 278b, and more preferably six. In addition, a plurality of body anchoring barbs 280 is disposed at regular intervals around the body 274. These barbs 280 may be small portions of the body 174 stamped into spikes and bent outward from the body 274. The barbs 280 desirably have a length of about 1 mm. FIGS. 11B and 11C illustrate a two-way lockout structure on the side edges 276a, 276b including tabs 282 and receptacles 284. In addition, alignment tabs 286 and slots 288 are provided as described above.

FIG. 12 shows the primary stent 270 of FIGS. 11A-11E coupled to an alternative secondary stent 290. The secondary stent 290 has relatively large, semi-circular sinus apertures 292 and membrane attachment strips 294 on its inner surface. Note that the sinus apertures 292 have a curvilinear cusp edge 296 that coincides approximately with an end edge 278b of the primary stent 270. This maximizes exterior reinforcement for the secondary stent 290 without interfering with the motion of the leaflet-forming membranes (not shown).

Figure 13A:
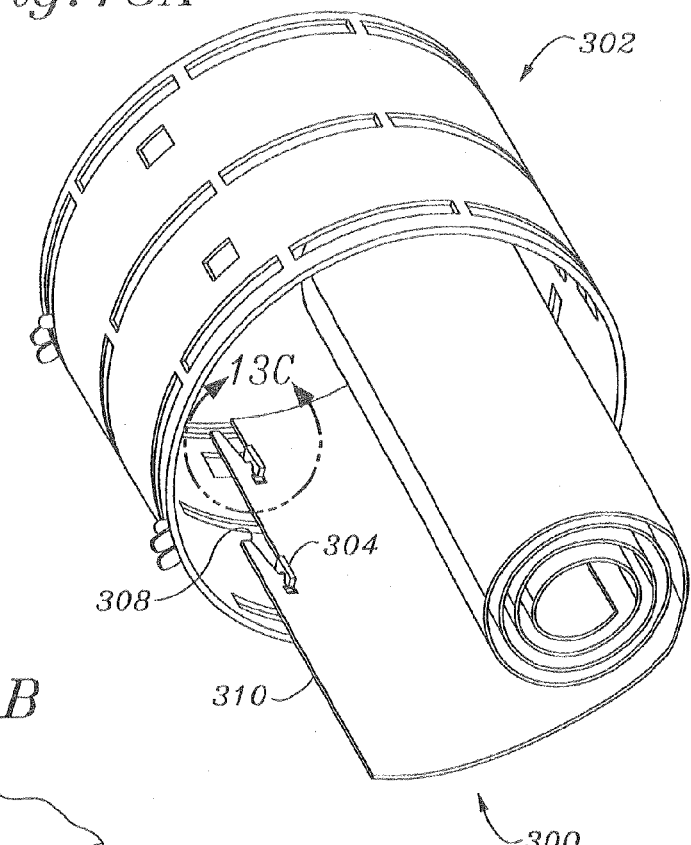
FIG. 13A is a perspective view of a schematic secondary stent being coupled to and unrolled within an expanded primary stent like that shown in FIG. 6A.
Figure 13B:
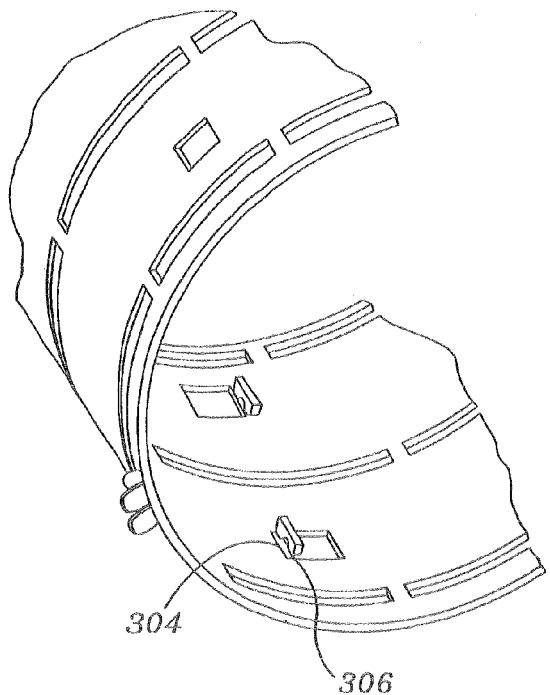
FIGS. 13B and 13C are detailed perspective views of the primary and secondary stent coupling shown in FIG. 13A.
Figure 13C:
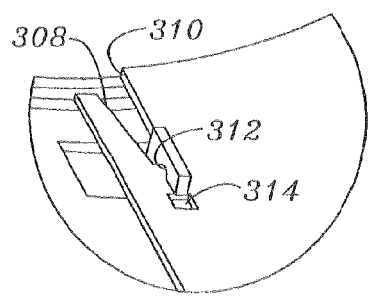
Figure 14:
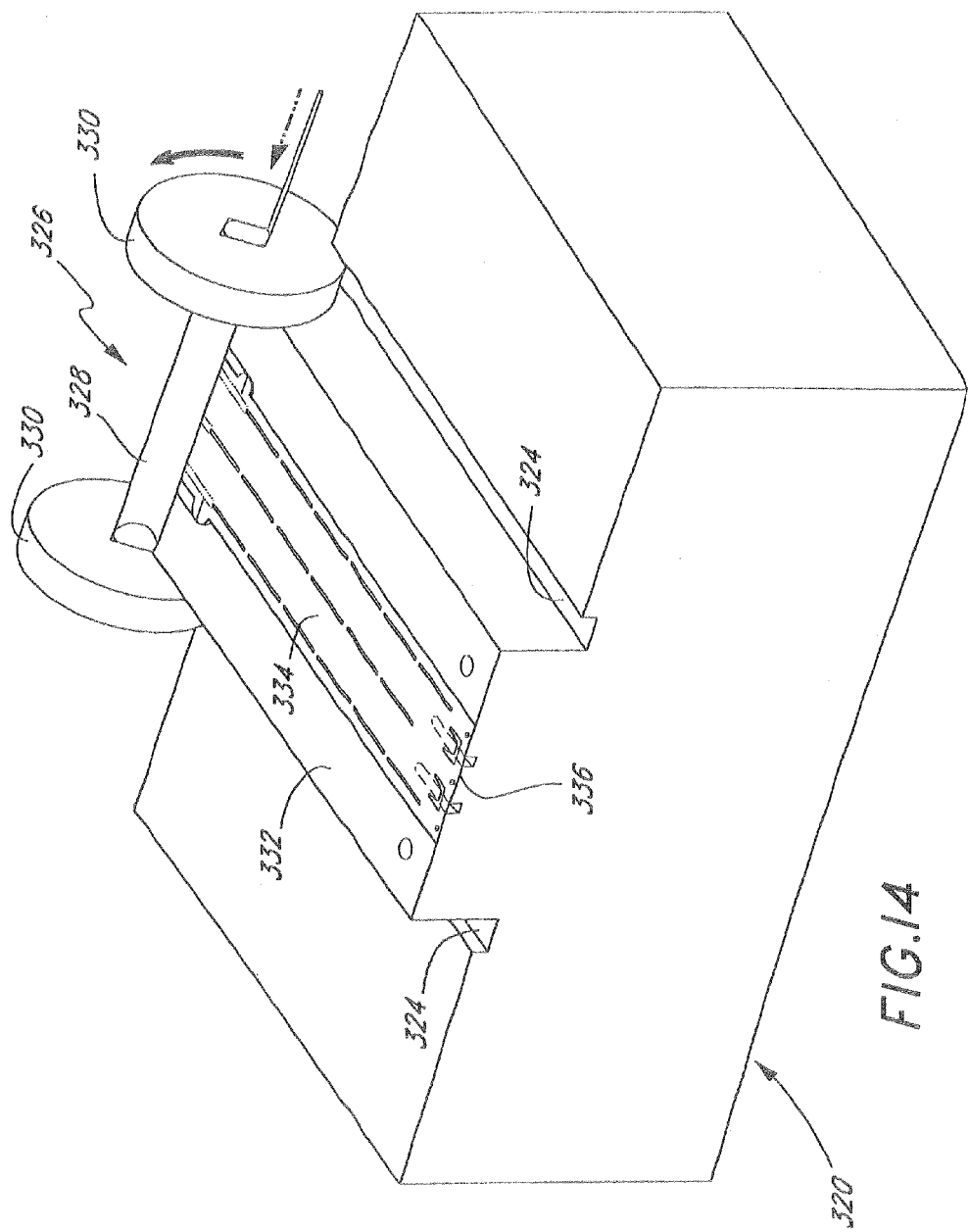
FIG. 14 is a schematic perspective view of an exemplary stent rolling apparatus of the present invention.

FIGS. 13A-13C schematically illustrate a secondary stent 300 unfurling within a primary stent 302. The primary stent 302 includes coupling tabs 304 bent inward from the body of the stent that have an axially-opening notch 306 on one side. The tabs 304 are slightly circumferentially offset with respect to one another, and axially spaced nearly the entire axial dimension of the primary stent 302. As best seen in FIG. 13C, the secondary stent 300 has a pair of V-shaped slots 308 located on a first side edge 310 that couple with the tabs 304. More specifically, the slots 308 terminate in a bridge 312 between the slot and a cutout 314, and the coupling tab 304 is designed to frictionally engage the bridge by virtue of the shape of the notch 306. The first side edge 310 is thus unrolled and the tabs 304 coupled to the slots 308 by a relative axial displacement of the secondary stent 300 and primary stent 302. Once coupled, the secondary stent 300 is fully unfurled and locked in its expanded configuration within the primary stent 302. The secondary stent 300 may be coupled to the primary stent 302 using relative axial and/or circumferential motion with or without a tactile feedback signaling completion of the coupling operation.

FIGS. 14-18 illustrate various steps in the process of rolling a primary stent of the present invention (i.e., converting a flat sheetlike material into the first, contracted configuration of the stent). A rolling base 320 includes a raised rolling platform 322 surrounded by a pair of linear rolling tracks 324. A stent roller 326 includes a central mandrel 328 and a pair of rolling wheels 330 that ride within the tracks 324.

An initially flat sheet-like primary stent 334 is placed on the rolling platform 322 and secured thereto at a first side edge 336. FIG. 15C illustrates one means for securing the first side edge 336, that is, angled pins 338 through holes in the first end. Alternatively, a clamp 340 as seen in FIG. 16 may be tightened over the first side edge 336.

With reference to FIGS. 15A and 15B, the stent roller 326 is temporarily secured to a second side edge using a pin 342 aligned with the mandrel 328. A plurality of lockout tabs 344 are seen projecting between the pin 342 and the mandrel 328 such that rotation of the roller 326 lifts the second side edge upward from the platform 322. The pin 342 extends through a small cavity in both rolling wheels 330 adjacent the mandrel 328 and may be easily removed once the rolling operation is complete.

FIG. 17A shows the stent 334 in its rolled configuration after the stent roller 326 has translated the length of the rolling platform 322. The rolling tracks 324 are slightly ramped upward toward the platform 322 to accommodate the gradually increasing diameter of the stent 334 as it is rolled. A plurality of linear grooves 350 in the rolling platform 322 provide clearance for any radially outwardly projecting tabs on the stent 334. FIG. 17B shows a suture 352 or other such retaining means tied around the rolled stent 334 to enable removal of the stent and roller 326 from the platform 322.

Finally, FIGS. 18A and 18B schematically illustrate the steps for removing the rolled stent 334 from the roller 326. Specifically, one of the wheels 330 is removable and the rolled stent 334 is then freed for use. The inner bore illustrated may be substantially smaller if a smaller mandrel 328 is used. The same sequence of rolling may be used for both the primary and secondary stents with the membranes. The membranes lie relatively flat against the secondary stents and present little obstacle to rolling.

The rolled stent 334 desirably has a diameter of less than about 20 mm. An aspect ratio of the stents of the present invention may be defined as the axial length over the final, expanded diameter. Some of the primary stents as described above may have a relatively small aspect ratio, desirably less than about 2.

Once the rolled stent 334 is formed, it is loaded within a delivery tube or catheter and urged down the tube to the implantation site (of course, the suture 352 will be removed). A pusher or other such device may be used to advance the rolled stent 334. Once at the site, the tube may be retracted and the rolled stent 334 caused to unfurl on its own, the stent may be delivered over an inflation balloon to enable plastic deformation/expansion, or the stent may be expanded with a subsequently introduced balloon or mechanical expander.

Figure 19:
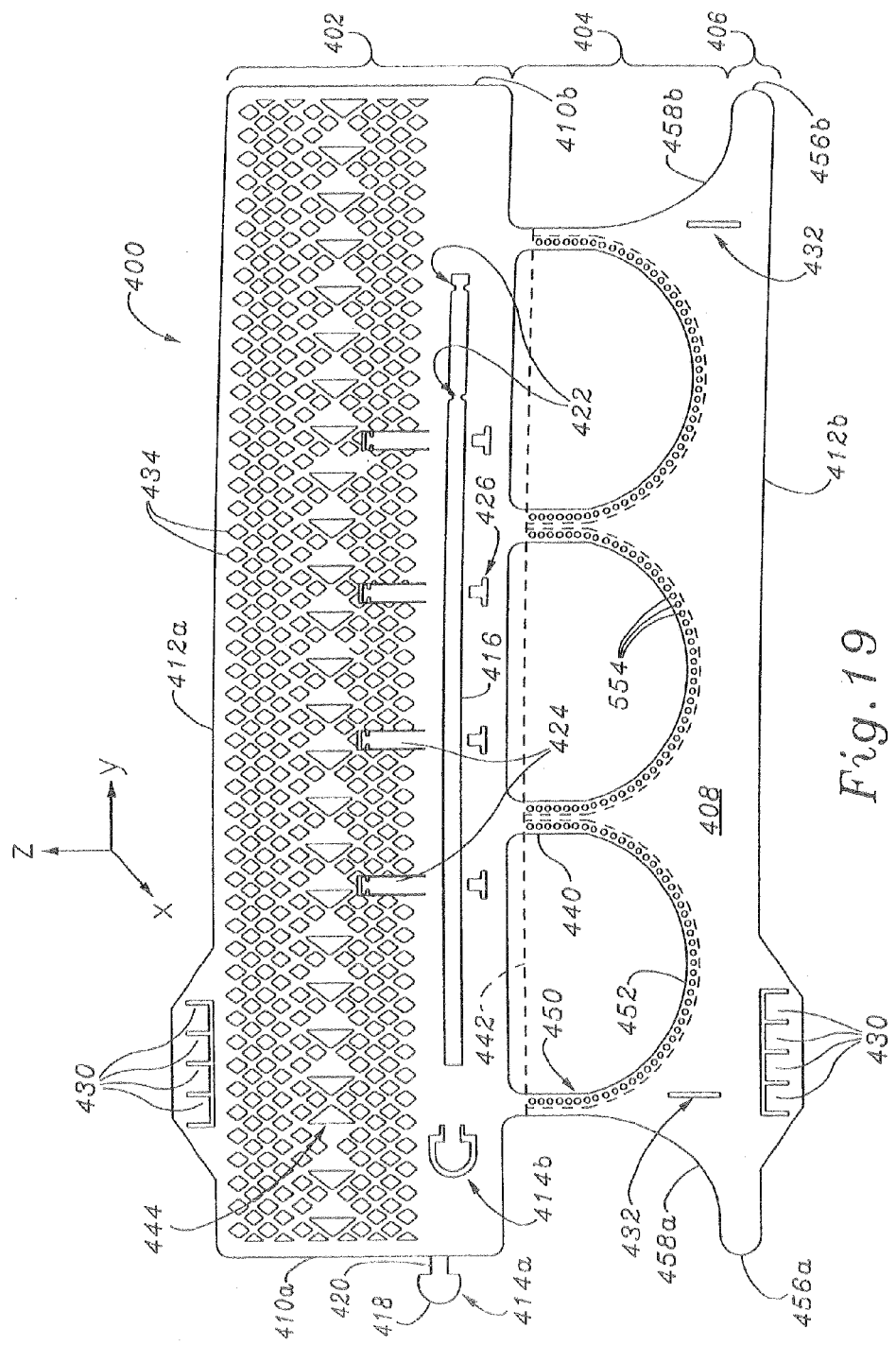
FIG. 19 is a plan view of a still further one-piece expandable heart valve stent of the present invention having a more solid outflow section.

FIG. 19 illustrates a still further one-piece expandable heart valve stent 400 of the present invention in its flattened configuration having a somewhat more solid or robust outflow section 402 than shown previously coupled to a sinus section 404 and anchoring section 406 on the inflow end of the stent. The stent 400 comprises a single sheet-like body 408 of a rolled superelastic metal alloy, preferably Nitinol. For orientation purpose, the body 408 is initially formed in the Y-Z plane as shown, and is elongated in the Y direction with a generally rectangular outline. The body 408 is designed to be rolled up on itself about a Z-axis into a relatively tight spiral, and later unrolled to form a tube with a first side edge 410a connecting to a second side edge 410b. In the illustrated embodiment, the left side of the stent body 408 forms the inner winding of the spiral while the right side is the outer winding. Desirably, and as mentioned above, the first side edge 410a and second side edge 410b overlap in the enlarged tubular configuration The body 408 also defines relatively linear first and second end edges 412a, 412b that form the circular outflow and inflow rims, respectively, of the tubular stent.

The stent 400 includes alignment structure for ensuring proper unrolling about the central Z-axis, and also locking structure for maintaining the final tubular shape. Specifically, a pair of guide/lockout tabs 414a, 414b engage a guide slot 416 that extends along the Y-axis in the outflow section, closely adjacent the sinus section 404. A single such guide slot 416 as shown located generally in the center of the body 408 with respect to the Z-axis is believed sufficient to hold the stent in the final tubular shape, although two or more may be used as described previously. The guide/lockout tabs 414a, 414b each include an enlarged generally semi-circular head 418 and a narrow neck 420 connecting the head to the body 408. A first tab 414a extends from the first end edge 410a while a cutout in a mid-portion of the body 408 forms a second tab 414b.

The spaced tabs 414a, 414b align with the guide slot 416 and are annealed out of the plane of the body 408 so as to fit within the slot. Specifically, the tabs 414a, 414b are annealed so that they bend inward with respect to the rolled spiral of the stent body 408 and can then be introduced into the slot 416. Once in the slot 416, the head 418 of each tab 414a, 414b projects through to the outside of the body 408 and retains the tabs in engagement with the slot. The neck 420 has a width that is slightly smaller than the slot width for easy longitudinal movement therewithin As the stent body 408 unfurls from its tightly coiled contracted state to its expanded state, the tabs 414a, 414b travel along the slot 416 (from the left to the right in the drawing). As this process occurs, the maintenance of the tabs 414a, 414b within the slot 416 ensures that the stent body 408 will not misalign and unroll into a conical shape. Ultimately, the tabs 414a, 414b travel past two pairs of similarly spaced lockout notches 422 annealed out of the plane of the body 408 toward the inside of the now tubular stent The interference between these lockout notches 422 and the heads 418 of the tabs 414a, 414b retains the stent 400 in its open, expanded configuration.

A plurality of engaging pairs of bridge tabs 424 and apertures 426 maintain a uniform width of the guide slot 416 to retain the tabs 414a, 414b therein during unrolling of the stent body 408. Each tab 424 is annealed so as to bend and lock into the corresponding aperture 426. Maintenance of the guide slot 416 width ensures a continuous engagement of the tabs 414a, 414band guide slot 416 during the unrolling process.

The stent body 408 further includes a plurality of edge tabs 430 located along both end edges 412a, 412b adjacent the first side edge 410a. Although shown flattened in the plane of the stent body 408, the edge tabs 430 are also annealed to bend generally perpendicular to the stent body. The edge tabs 430 are disposed closely to and constrain the end edges 412a, 412b during the unrolling process to further help prevent misalignment. A pair of stop slots 432 is formed in the anchor section 406 to limit the extent that the stent body 408 unrolls. One side of each slot 432 is annealed out of the plane of the stent body 408 so that they engage each other after the body has unrolled to the tubular final shape.

The outflow section 402 includes an array of diamond-shaped apertures 434 forming an open lattice, mesh or grid pattern that reduces the stent surface area and thus the risk of thrombosis after implantation. The open mesh pattern is somewhat stiffer than, for example, the grid pattern shown in the stent of FIG. 1, and helps stabilize the valve commissures 440 about which flexible leaflet membranes 442 (shown in phantom) are attached. A plurality of triangular-shaped cutouts 444 aligned in the Y-direction in the outflow section 402 "ratchet" against one another during unrolling of the stent body 408 and thus incrementally prevent closing of the stent.

Still with reference to FIG. 19, the sinus section 404 incorporates three membrane apertures 450 defining the aforementioned commissures 440 and intermediate curvilinear cusps 452. A series of attachment holes 454 closely surrounds each aperture 450 and is used to suture or otherwise attach each membrane 442 to the stent 400. The edge of each membrane 442 is folded as described above with respect to FIG. 2B to help prevent wear and ensure longevity. The opposed ends of the sinus section 404 are shaped to conform to the outer two membrane apertures 450. That is, a pair of opposed extension flaps 456a, 456b on the anchoring section 406 overlap and each blends along a curvilinear edge 458a, 458b toward the outflow section 402. These curvilinear edges 458a, 458b provide reliefs to avoid occluding either of the outer two membrane apertures 450 when the stent is locked open and the flaps 456a, 456b overlap.

Although not shown, a plurality of anchoring barbs are desirably provided in at least the anchoring section 406 to secure the unrolled valve into position in the valve annulus and aortic root. Further, the outflow section 402 may be annealed so as to flare outward and contact the ascending aorta for further anchoring.

FIG. 20A illustrates a still further one-piece expandable heart valve stent 500 of the present invention in its flattened configuration with an outflow section 502 coupled to a sinus section 504 and anchoring section 506 on the inflow end of the stent. The stent 500 again comprises a single sheet-like body 508 of a rolled superelastic metal alloy, preferably Nitinol. For orientation purpose, the body 508 is initially formed in the Y-Z plane as shown, and is elongated in the Y direction with a generally rectangular outline. The body 508 is designed to be rolled up on itself about a Z-axis into a relatively tight spiral, and later unrolled to form a tube with a first side edge 510a connecting to a second side edge 510b. In the illustrated embodiment, the left side of the stent body 508 forms the inner winding of the spiral while the right side is the outer winding. That is, the stent body 508 is rolled from the left end in the direction of arrow 511. Desirably, the first side edge 510a and second side edge 510b overlap in the enlarged tubular configuration. The body 508 also defines first and second end edges 512a, 512b that form the circular outflow and inflow ends, respectively, of the tubular stent.

The stent 500 includes alignment structure for ensuring proper unrolling about the central Z-axis, and also locking structure for maintaining the final tubular shape. Specifically, guide/lockout tabs 514a, 514b engage guide slots 516a, 516b aligned therewith along the Y-axis. A first pair of tab 514a and slot 516a is located in the outflow section, closely adjacent the sinus section 504, while a second pair of tab 514b and slot 516b is located in the anchoring section, closely adjacent the second end edge 512b. The guide/lockout tabs 514a, 514b are each formed with an enlarged head 518 and a pair of necks 520 on either side of the head connecting it to the body 508. Each head 518 is annealed to bend about the necks 520 out of the plane of the stent body 508 and fits through an entrance opening 522 into the respective slot 516. In the illustrated embodiment, the heads 518 are bent out of the page and the stent body 508 is rolled about the Z-axis out of the page so that the heads 518 project radially outwardly through the entrance openings 522.

As seen in FIGS. 20A and 20B, each slot 516 includes a pair of lockout tabs 524 near the slot end closest to the second end edge 510b. Small angled cutouts 526 diverging on either side of the slot 516 form the lockout tabs 524. Each tab 524 is annealed to bend out of the plane of the stent body 508, in this case into the page. As the stent body 508 unrolls, the heads 518 of the tabs 514a, 514b slide from left to right along the slots 516 and cam over the bent tabs 524. The tabs 514a, 514b are thus prevented by the tabs 524 from retreating along the slots 516a, 516b. The maintenance of the tabs 514a, 514b within the slots 516a, 516b ensures that the stent body 508 will not misalign and unroll into a conical shape.

A plurality of bridges 528 maintains a uniform width of the guide slots 516a, 516b to retain the tabs 514a, 514b therein during unrolling of the stent body 508. Each bridge 528 crosses over the respective slot 516a, 516b and is secured thereto at points 530, such as by ultrasonic welding. Alternatively, bridges formed as an integral part of the stent body 508 are contemplated. Maintenance of the guide slot 516 width ensures a continuous engagement of the tabs 514a, 514b and guide slots 156a, 516b during the unrolling process. The bridges 528 are located on the inner side of the stent 508 in its rolled configuration.

The outflow section 502 includes an array of cross members 534 forming a lattice, mesh or grid pattern with diamond-shaped openings that reduces the stent surface area and thus the risk of thrombosis after implantation. Adjacent the mesh pattern, a solid band 536 of the stent body 508 within which the guide slot 516a is formed helps stabilize the valve commissures 540 about which flexible leaflet membranes 542 (shown in phantom) are attached.

Still with reference to FIG. 20A, the sinus section 504 incorporates three membrane apertures 550 defining the aforementioned commissures 540 and intermediate curvilinear cusps 552. A series of attachment holes 554 closely surrounds each aperture 550 and is used to suture or otherwise attach each membrane 542 to the stent 500. The edge of each membrane 542 is folded as described above with respect to FIG. 2B to help prevent wear and ensure longevity. The right end of the sinus section 504 is shaped to conform to the left membrane apertures 550. That is, a curvilinear edge 558 provides a relief to avoid occluding the left membrane aperture 550 when the stent is locked open and the end edges 510a, 510b overlap.

Although not shown, a plurality of anchoring barbs are desirably provided in at least the anchoring section 506 to secure the unrolled valve into position in the valve annulus and aortic root. Further, the outflow section 502 may be annealed so as to flare outward and contact the ascending aorta for further anchoring.

FIGS. 21A illustrates a heart valve 600 of the present invention having a stent 602 similar to the stent 500 described above with reference to FIG. 20A. A pair of lockout/guide tabs 604a, 604b engages an aligned pair of guide slots 604a, 604b to both ensure proper unrolling and secure the unrolled valve in its expanded configuration. The tabs 604a, 604b and slots 606a, 606b may be configured as described above with respect to either of the embodiments of FIG. 19 or 20A, or may be a similar expedient. In this regard, entrance openings 608 and lockout tabs 610 may be provided to enable the tabs 604a, 604b to enter the slots 606a, 606b and be retained therein in an open, unrolled configuration of the valve 600. A plurality of bridges 612 seen on the inside of the stent 602 through the slots 606a, 606b maintain the width of the slots as described above.

The stent 602 includes an outflow section 620 having a mesh 622 that is annealed to flare outward into contact with the aorta and increase the stiffness of valve commissures in a sinus section 624. She sinus section 624 includes three membranes 626 attached around generally semi-circular apertures 628 to form the occluding surfaces of the valve when fully unrolled.

FIG. 21B illustrates the stent 602 by itself in a partial state of unrolling, while FIG. 21C shows the stent fully unrolled. Note the flared configuration of the mesh 622 on the outflow section 620 and the overlapped sides of the stent.

FIGS. 22 and 23 illustrate two different two-piece expandable heart valve stents that are coupled using guide wires. In FIG. 22, a generally tubular primary stent 700 is first unrolled and implanted in the body. A secondary stent 702 of various configurations described above is then delivered in its contracted state into proximity with the primary stent 700 and unrolled and coupled thereto. To ensure proper rotational alignment between the primary stent 700 and secondary stent 702, a plurality of guide wires 704 are threaded through features (not shown) within the secondary stent 702 and coupled to corresponding features on the primary stent 700. For example, the guide wires 704 may be threaded or otherwise registered with coupling tabs (not shown) on the secondary stent 702 and also with coupling apertures 706 on the primary stent 700. In this way, the secondary stent 702 advances along the guide wires 704 and is rotationally oriented thereby to ensure mating engagement of the coupling features. The distal end of a delivery tube 708 is illustrated through which the guide wires 704 are pulled.

FIG. 23 likewise shows a generally tubular primary stent 720 being coupled to a secondary stent 722 using a plurality of guide wires 724. The secondary stent 722 includes a tubular mesh portion 726 and a scalloped wireform portion 728 on an outflow end. Although not shown, the wireform portion 728 receives valve leaflets or an intact bioprosthetic valve as is well known in the art. The tubular mesh portion 726 fits within and couples to the tubular primary stent 720, while the wireform portion 728 remains completely or substantially completely extended out of the outflow end of the primary stent. Again, the distal end of a delivery tube 730 is illustrated.

The heart valves of the present invention may be implanted using several minimally-invasive approaches, and in one or more stages. For example, the single stent valves described herein may be delivered using a pusher or along with a balloon catheter through a large bore cannula or catheter (i.e., tube). The two piece valves may be delivered through a single tube, or through two different tubes in sequence. In one embodiment, the stent having the flexible membranes thereon may be stored in an unfurled configuration to reduce stress on and damage to the membranes, and rolled into a compact tube just prior to use. One or two balloons may be used, or the stents can be primarily self-expanding with a balloon or other expansion device used to provide a final deployment force, such as for anchoring barbs in the annulus or locking the rolled stents in the open configuration.

While the foregoing describes the preferred embodiments of the invention, various alternatives, modifications, and equivalents may be used. Moreover, it will be obvious that certain other modifications may be practiced within the scope of the appended claims.

What is claimed is:

1. A two-part prosthetic heart valve, comprising:
an expandable tubular primary stent sized to contact a heart valve annulus in an expanded state and having a first plurality of discrete mating features, wherein the tubular primary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the patient's heart valve annulus from within;
an expandable secondary stent configured to be coupled to the primary stent and having a second plurality of discrete mating features that mate with the first plurality of discrete mating features on the primary stent;
a plurality of valve leaflets attached to the secondary stent for occluding blood flow in one direction; and
a plurality of guidewires each threaded through the secondary stent and then coupled to the primary stent for ensuring proper rotational alignment during advancement of the secondary stent toward the primary stent so that the first and second pluralities of discrete mating features on both the primary stent and secondary stent engage each other.

2. The two-part prosthetic heart valve of claim 1, wherein the expandable secondary stent has a tubular mesh portion and a scalloped wireform portion, wherein the valve leaflets attach to the wireform portion.

3. The two-part prosthetic heart valve of claim 2, wherein the tubular mesh portion is configured to fit within and couple to the tubular primary stent while the wireform portion extends out of an outflow end of the primary stent.

4. The two-part prosthetic heart valve of claim 1, wherein the second plurality of discrete mating features on the secondary stent comprise coupling tabs and the first plurality of discrete mating features on the primary stent comprise coupling apertures.

5. The two-part prosthetic heart valve of claim 1, wherein the valve leaflets include separate leaflets cut from bovine pericardium and the secondary stent has a scalloped wireform portion on an outflow end thereof, the wireform portion having alternating arcuate cusps and upstanding commissures that support the separate leaflets.

6. The two-part prosthetic heart valve of claim 1, wherein the expandable secondary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the tubular primary stent from within.

7. The two-part prosthetic heart valve of claim 1, wherein the tubular primary stent is balloon expandable.

8. The two-part prosthetic heart valve of claim 1, wherein the secondary stent is balloon expandable.

9. A two-part prosthetic heart valve, comprising:
an expandable tubular primary stent sized to contact a heart valve annulus in an expanded state and having a first plurality of discrete mating features;
an expandable secondary stent configured to be coupled to the primary stent and having a second plurality of discrete mating features that mate with the first plurality of discrete mating features on the primary stent, wherein the expandable secondary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the tubular primary stent from within;
a plurality of valve leaflets attached to the secondary stent for occluding blood flow in one direction; and
a plurality of guidewires each threaded through the secondary stent and then coupled to the primary stent for ensuring proper rotational alignment during advancement of the secondary stent toward the primary stent so that the first and second pluralities of discrete mating features on both the primary stent and secondary stent engage each other.

10. A method of delivering a two-part prosthetic heart valve, comprising:
providing an expandable tubular primary stent sized to contact a heart valve annulus in an expanded state and having a first plurality of discrete mating features;
providing an expandable secondary stent configured to be coupled to the primary stent and having a second plurality of discrete mating features that mate with the first plurality of discrete mating features on the primary stent to couple the secondary stent thereto, wherein the expandable secondary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the tubular primary stent from within;
providing a plurality of guidewires each threaded through the secondary stent and then coupled to the primary stent to ensure proper rotational alignment between the secondary stent and the primary stent;
expanding the primary stent within the heart valve annulus; and
advancing the secondary stent along the guidewires so that the first and second pluralities of discrete mating features on both the primary stent and secondary stent engage each other and the secondary stent couples to the primary stent.

11. A method of delivering a two-part prosthetic heart valve, comprising:
providing an expandable tubular primary stent sized to contact a heart valve annulus in an expanded state and having a first plurality of discrete mating features, wherein the tubular primary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the patient's heart valve annulus from within;
providing an expandable secondary stent configured to be coupled to the primary stent and having a second plurality of discrete mating features that mate with the first plurality of discrete mating features on the primary stent to couple the secondary stent thereto;
providing a plurality of guidewires each threaded through the secondary stent and then coupled to the primary stent to ensure proper rotational alignment between the secondary stent and the primary stent;
expanding the primary stent within the heart valve annulus; and
advancing the secondary stent along the guidewires so that the first and second pluralities of discrete mating features on both the primary stent and secondary stent engage each other and the secondary stent couples to the primary stent.

12. The method of claim 11, wherein the secondary stent has a tubular mesh portion and a scalloped wireform portion and wherein a valve member is attached to the wireform portion for occluding blood flow in one direction.

13. The method of claim 12, wherein the tubular mesh portion is configured to couple to the tubular primary stent while the wireform portion extends out of an outflow end of the primary stent.

14. The method of claim 12, wherein the valve member includes separate leaflets cut from bovine pericardium and the secondary stent has a scalloped wireform portion on an outflow end thereof, the wireform portion having alternating arcuate cusps and upstanding commissures that support the separate leaflets.

15. The method of claim 11, wherein the second plurality of discrete mating features on the secondary stent comprise coupling tabs and the first plurality of discrete mating features on the primary stent comprise coupling apertures.

16. The prosthetic heart valve delivery method of claim 11 wherein the expandable secondary stent comprises a stent body having a first, contracted configuration in which the stent body is spirally-wound about an axis such that at least one winding of the stent body overlaps another winding, and a second, expanded configuration in which the stent body is substantially unwound and at least partly forms a tube centered about the axis and sized to engage the tubular primary stent from within.

17. The prosthetic heart valve delivery method of claim 11, wherein the tubular primary stent is balloon expandable.

18. The prosthetic heart valve delivery method of claim 11, wherein the secondary stent is balloon-expandable.

* * * * *